United States Patent
Smith et al.

(10) Patent No.: US 9,615,866 B1
(45) Date of Patent: Apr. 11, 2017

(54) SURGICAL FIXATION SYSTEM AND RELATED METHODS

(75) Inventors: William Smith, Las Vegas, NV (US); Chad Grant, San Diego, CA (US); Richard Mueller, Carlsbad, CA (US); Eric Dasso, Encinitas, CA (US); Christopher Huntington, Providence, RI (US); Christopher Campbell, Temecula, CA (US)

(73) Assignee: NuVasive, Inc., San Diego, CA (US)

( * ) Notice: Subject to any disclaimer, the term of this patent is extended or adjusted under 35 U.S.C. 154(b) by 797 days.

(21) Appl. No.: 12/364,507

(22) Filed: Feb. 2, 2009

Related U.S. Application Data

(60) Provisional application No. 61/025,702, filed on Feb. 1, 2008.

(51) Int. Cl.
*A61B 17/80* (2006.01)

(52) U.S. Cl.
CPC ................ *A61B 17/8052* (2013.01)

(58) Field of Classification Search
CPC ... A61B 17/808; A61B 17/80; A61B 17/8004; A61B 17/8009; A61B 17/8014; A61B 17/8019; A61B 17/8023; A61B 17/8028; A61B 17/8052; A61B 17/8061; A61B 17/8066; A61B 17/8071; A61B 17/8076
USPC ......................................... 606/280–299, 305
See application file for complete search history.

(56) References Cited

U.S. PATENT DOCUMENTS

| | | | |
|---|---|---|---|
| 2,406,832 A | 9/1946 | Hardinge | |
| 2,486,303 A | 10/1949 | Longfellow | |
| 2,922,456 A | 1/1960 | Kann | |
| 3,463,148 A * | 8/1969 | Treace | 606/286 |
| 4,388,921 A | 6/1983 | Sutter | |
| 4,484,570 A | 11/1984 | Sutter | |
| 4,696,290 A | 9/1987 | Steffee | |
| 4,836,196 A | 6/1989 | Park et al. | |
| 4,913,134 A | 4/1990 | Luque | |
| 5,057,111 A | 10/1991 | Park | |
| 5,084,049 A | 1/1992 | Asher et al. | |
| 5,108,395 A | 4/1992 | Laurain | |
| 5,129,903 A | 7/1992 | Luhr | |
| 5,147,363 A | 9/1992 | Harle | |
| 5,209,751 A | 5/1993 | Farris et al. | |

(Continued)

FOREIGN PATENT DOCUMENTS

| | | |
|---|---|---|
| CH | 672245 A5 | 11/1989 |
| EP | 0293411 | 12/1988 |

(Continued)

*Primary Examiner* — Lynnsy Summitt
(74) *Attorney, Agent, or Firm* — Jeremy A. Smith; Michele P. Marron; Bradley Arant Boult Cummings LLP

(57) ABSTRACT

A surgical fixation system including a base plate, a plurality of anchors, and a plurality of locking elements. The base plate has a pair of fixation apertures configured to receive at least a portion of the anchors therethrough. The fixation apertures are provided by example as elongated slots. The fixation apertures are located within the base plate such that upon proper placement of the base plate within a surgical target site, one of the fixation apertures is positioned over a first bone segment (e.g. a first vertebral body), and the other fixation aperture is positioned over a second bone segment (e.g. a second vertebral body).

9 Claims, 24 Drawing Sheets

(56) References Cited

U.S. PATENT DOCUMENTS

| | | |
|---|---|---|
| 5,234,431 A | 8/1993 | Keller |
| 5,261,910 A * | 11/1993 | Warden et al. ............... 606/292 |
| 5,275,601 A | 1/1994 | Gogolewski et al. |
| 5,290,288 A | 3/1994 | Vignaud et al. |
| 5,423,826 A * | 6/1995 | Coates et al. .................. 606/96 |
| 5,534,027 A | 7/1996 | Hodorek |
| 5,534,032 A | 7/1996 | Hodorek |
| 5,549,612 A | 8/1996 | Yapp |
| 5,603,713 A | 2/1997 | Aust |
| 5,607,426 A | 3/1997 | Ralph |
| 5,616,142 A | 4/1997 | Yuan |
| 5,616,144 A | 4/1997 | Yapp |
| 5,634,926 A | 6/1997 | Jobe |
| 5,676,666 A | 10/1997 | Oxland et al. |
| 5,728,099 A | 3/1998 | Tellman |
| 5,735,853 A | 4/1998 | Olerud |
| 5,800,433 A | 9/1998 | Benzel |
| 5,827,286 A | 10/1998 | Incavo |
| 5,902,303 A | 5/1999 | Eckhof |
| 5,902,304 A | 5/1999 | Walker |
| 5,954,722 A | 9/1999 | Bono |
| 5,964,761 A | 10/1999 | Kambin |
| 5,964,762 A | 10/1999 | Biedermann |
| 6,017,345 A | 1/2000 | Richelsoph |
| 6,030,389 A | 2/2000 | Wagner |
| 6,039,740 A | 3/2000 | Olerud |
| 6,117,173 A | 9/2000 | Taddia |
| 6,159,213 A | 12/2000 | Rogozinski |
| 6,183,476 B1 | 2/2001 | Gerhardt |
| 6,228,085 B1 | 5/2001 | Theken |
| 6,235,033 B1 | 5/2001 | Brace |
| 6,241,731 B1 | 6/2001 | Fiz |
| 6,258,089 B1 | 7/2001 | Campbell |
| 6,261,291 B1 | 7/2001 | Talaber |
| 6,273,889 B1 | 8/2001 | Richelsoph |
| 6,280,445 B1 | 8/2001 | Johnson |
| 6,302,883 B1 * | 10/2001 | Bono ............................. 606/291 |
| 6,306,136 B1 | 10/2001 | Baccelli |
| 6,309,393 B1 | 10/2001 | Tepic |
| 6,315,779 B1 | 11/2001 | Morrison et al. |
| 6,331,179 B1 | 12/2001 | Freid |
| 6,355,038 B1 | 3/2002 | Pisharodi |
| 6,383,186 B1 | 5/2002 | Michelson |
| 6,402,756 B1 | 6/2002 | Ralph |
| 6,428,542 B1 | 8/2002 | Michelson |
| 6,454,769 B2 | 9/2002 | Wagner |
| 6,533,786 B1 | 3/2003 | Needham |
| 6,575,975 B2 | 6/2003 | Brace |
| 6,592,586 B1 | 7/2003 | Michelson |
| 6,626,907 B2 | 9/2003 | Campbell |
| 6,641,583 B2 * | 11/2003 | Shluzas et al. ............... 606/252 |
| 6,645,208 B2 | 11/2003 | Apfelbaum |
| 6,689,134 B2 | 2/2004 | Ralph |
| D493,533 S | 7/2004 | Blain |
| 6,793,658 B2 | 9/2004 | LeHuec |
| 6,858,031 B2 | 2/2005 | Morrison et al. |
| 6,884,242 B2 | 4/2005 | LeHuec |
| 6,969,390 B2 | 11/2005 | Michelson |
| 7,001,389 B1 | 2/2006 | Navarro |
| 7,041,105 B2 | 5/2006 | Michelson |
| 7,044,952 B2 | 5/2006 | Michelson |
| 7,094,238 B2 | 8/2006 | Morrison |
| 7,097,645 B2 | 8/2006 | Michelson |
| 7,112,202 B2 | 9/2006 | Michelson |
| D530,423 S | 10/2006 | Miles |
| 7,118,573 B2 | 10/2006 | Michelson |
| 7,135,024 B2 | 11/2006 | Cook |
| 7,137,984 B2 | 11/2006 | Michelson |
| 7,175,624 B2 | 2/2007 | Konieczynski |
| 7,186,254 B2 | 3/2007 | Dinh |
| 7,189,237 B2 * | 3/2007 | Huebner ...................... 606/291 |
| 7,214,226 B2 | 5/2007 | Alleyne |
| 7,229,443 B2 | 6/2007 | Eberlein |
| 7,232,670 B2 | 6/2007 | D'Azzo |
| 7,309,340 B2 | 12/2007 | Fallin |
| 7,318,825 B2 | 1/2008 | Butler |
| 7,326,212 B2 | 2/2008 | Huebner |
| 7,331,961 B2 | 2/2008 | Abdou |
| D594,986 S | 6/2009 | Miles |
| D599,019 S | 8/2009 | Pimenta |
| 7,608,096 B2 | 10/2009 | Foley et al. |
| 7,621,914 B2 | 11/2009 | Ralph |
| 7,635,364 B2 | 12/2009 | Barrall |
| 7,635,366 B2 | 12/2009 | Abdou |
| 7,637,928 B2 | 12/2009 | Fernandez |
| 7,648,506 B2 * | 1/2010 | McCord et al. ............ 606/86 A |
| 7,658,754 B2 | 2/2010 | Zhang et al. |
| 7,670,360 B2 | 3/2010 | Catbagan et al. |
| 7,695,473 B2 | 4/2010 | Ralph |
| 7,740,630 B2 | 6/2010 | Michelson |
| D621,509 S | 8/2010 | Lovell |
| 7,857,839 B2 | 12/2010 | Duong |
| 7,901,440 B2 | 3/2011 | Ibrahim |
| 7,935,123 B2 | 5/2011 | Fanger |
| 7,951,151 B2 | 5/2011 | Butler |
| 8,002,809 B2 | 8/2011 | Baynham |
| 8,083,781 B2 | 12/2011 | Reimels |
| 8,182,533 B2 | 5/2012 | Perkins |
| 8,206,390 B2 | 6/2012 | Lindemann |
| 8,287,574 B2 | 10/2012 | Biyani |
| D671,645 S | 11/2012 | Curran |
| D674,092 S | 1/2013 | Lovell |
| D675,320 S | 1/2013 | Oi |
| 8,348,949 B2 | 1/2013 | Butler |
| 8,388,661 B2 * | 3/2013 | Schlaepfer et al. .......... 606/278 |
| 8,394,130 B2 | 3/2013 | Orbay |
| 8,500,783 B2 | 8/2013 | Baynham |
| 8,506,607 B2 | 8/2013 | Eckhof |
| D696,402 S | 12/2013 | Oi |
| 8,636,738 B2 | 1/2014 | McClintock |
| 8,728,127 B2 | 5/2014 | Stewart |
| 8,758,347 B2 | 6/2014 | Weiner |
| D708,747 S | 7/2014 | Curran |
| 8,784,419 B2 | 7/2014 | Overes |
| D711,537 S | 8/2014 | Pimenta |
| 8,915,918 B2 | 12/2014 | Graham |
| D721,808 S | 1/2015 | Oi |
| 2001/0014807 A1 | 8/2001 | Wagner |
| 2001/0021851 A1 | 9/2001 | Eberlein |
| 2002/0045898 A1 | 4/2002 | Freid |
| 2002/0058939 A1 | 5/2002 | Wagner |
| 2002/0147450 A1 | 10/2002 | LeHuec |
| 2002/0151899 A1 | 10/2002 | Bailey |
| 2002/0156474 A1 | 10/2002 | Wack |
| 2003/0078583 A1 | 4/2003 | Biedermann |
| 2003/0083658 A1 | 5/2003 | Hawkes |
| 2003/0093082 A1 | 5/2003 | Campbell |
| 2003/0135216 A1 | 7/2003 | Sevrain |
| 2003/0153919 A1 | 8/2003 | Harris |
| 2003/0187440 A1 | 10/2003 | Richelsoph |
| 2003/0187442 A1 | 10/2003 | Richelsoph |
| 2003/0187443 A1 | 10/2003 | Lauryssen |
| 2003/0208204 A1 | 11/2003 | Bailey |
| 2003/0229348 A1 | 12/2003 | Sevrain |
| 2004/0019353 A1 | 1/2004 | Freid |
| 2004/0030340 A1 | 2/2004 | Pisharodi |
| 2004/0073218 A1 | 4/2004 | Dahners |
| 2004/0087951 A1 | 5/2004 | Khalili |
| 2004/0097935 A1 | 5/2004 | Richelsoph |
| 2004/0106924 A1 | 6/2004 | Ralph |
| 2004/0127896 A1 | 7/2004 | Lombardo |
| 2004/0127899 A1 | 7/2004 | Konieczynski |
| 2004/0127900 A1 | 7/2004 | Konieczynski |
| 2004/0127904 A1 | 7/2004 | Konieczynski |
| 2004/0153078 A1 | 8/2004 | Grinberg |
| 2004/0158250 A1 | 8/2004 | Chappuis |
| 2004/0167521 A1 | 8/2004 | De Windt |
| 2004/0186570 A1 | 9/2004 | Rapp |
| 2004/0210223 A1 | 10/2004 | Pisharodi |
| 2004/0225290 A1 | 11/2004 | Ferree |
| 2004/0236333 A1 | 11/2004 | Lin |
| 2004/0245479 A1 | 12/2004 | Misawa |
| 2004/0260292 A1 | 12/2004 | Orbay |
| 2004/0260293 A1 | 12/2004 | Orbay |

(56) References Cited

U.S. PATENT DOCUMENTS

| | | |
|---|---|---|
| 2004/0260294 A1 | 12/2004 | Orbay |
| 2004/0260295 A1 | 12/2004 | Orbay |
| 2004/0260306 A1 | 12/2004 | Fallin |
| 2005/0010227 A1 | 1/2005 | Paul |
| 2005/0015092 A1 | 1/2005 | Rathbun |
| 2005/0015093 A1 | 1/2005 | Suh |
| 2005/0015131 A1 | 1/2005 | Fourcault |
| 2005/0027293 A1 | 2/2005 | LeHuec |
| 2005/0033298 A1 | 2/2005 | Hawkes |
| 2005/0049593 A1 | 3/2005 | Duong |
| 2005/0049595 A1 | 3/2005 | Suh et al. |
| 2005/0059970 A1 | 3/2005 | Kolb |
| 2005/0070904 A1 | 3/2005 | Gerlach |
| 2005/0096657 A1 | 5/2005 | Autericque et al. |
| 2005/0107796 A1 | 5/2005 | Gerlach |
| 2005/0131419 A1 * | 6/2005 | McCord et al. ............... 606/99 |
| 2005/0177160 A1 | 8/2005 | Baynham |
| 2005/0177161 A1 | 8/2005 | Baynham |
| 2005/0182404 A1 | 8/2005 | Lauryssen |
| 2005/0192580 A1 | 9/2005 | Dalton |
| 2005/0228386 A1 | 10/2005 | Ziolo |
| 2006/0015104 A1 | 1/2006 | Dalton |
| 2006/0100626 A1 | 5/2006 | Rathbun |
| 2006/0106387 A1 | 5/2006 | Fanger |
| 2006/0122602 A1 | 6/2006 | Konieczynski |
| 2006/0122604 A1 | 6/2006 | Gorhan |
| 2006/0149249 A1 | 7/2006 | Mathoulin |
| 2006/0149251 A1 | 7/2006 | Ziolo |
| 2006/0149253 A1 | 7/2006 | Doubler |
| 2006/0149255 A1 | 7/2006 | Doubler |
| 2006/0149256 A1 | 7/2006 | Wagner |
| 2006/0184170 A1 | 8/2006 | Kapitan et al. |
| 2006/0195085 A1 * | 8/2006 | Happonen et al. ............. 606/61 |
| 2006/0235399 A1 | 10/2006 | Carls |
| 2006/0241616 A1 | 10/2006 | Konieczynski |
| 2006/0241618 A1 | 10/2006 | Gasser |
| 2006/0247639 A1 | 11/2006 | Anderson |
| 2006/0271052 A1 | 11/2006 | Stern |
| 2006/0276793 A1 | 12/2006 | Berry |
| 2006/0293669 A1 | 12/2006 | Lindemann |
| 2007/0010817 A1 | 1/2007 | de Coninck |
| 2007/0118125 A1 | 5/2007 | Orbay |
| 2007/0123879 A1 | 5/2007 | Songer |
| 2007/0162020 A1 | 7/2007 | Gerlach |
| 2007/0260244 A1 | 11/2007 | Wolter |
| 2008/0004627 A1 | 1/2008 | Dalton |
| 2008/0009870 A1 | 1/2008 | Lombardo |
| 2008/0058817 A1 | 3/2008 | Eberlein |
| 2008/0097442 A1 | 4/2008 | Dixon |
| 2008/0147124 A1 | 6/2008 | Haidukewych |
| 2008/0147125 A1 | 6/2008 | Colleran |
| 2008/0177330 A1 | 7/2008 | Ralph |
| 2008/0228230 A1 | 9/2008 | Ferree |
| 2008/0234680 A1 | 9/2008 | Zaiser |
| 2008/0243192 A1 | 10/2008 | Jacene |
| 2008/0275510 A1 | 11/2008 | Schonhardt et al. |
| 2009/0012571 A1 | 1/2009 | Perrow |
| 2009/0018588 A1 | 1/2009 | Eckhof |
| 2009/0024170 A1 | 1/2009 | Kirschman |
| 2009/0036933 A1 | 2/2009 | Dube |
| 2009/0105755 A1 | 4/2009 | Capote |
| 2009/0163960 A1 | 6/2009 | Binder |
| 2009/0182383 A1 | 7/2009 | Prybyla |
| 2009/0192549 A1 | 7/2009 | Sanders |
| 2009/0192553 A1 | 7/2009 | Maguire |
| 2009/0210014 A1 | 8/2009 | Ziolo |
| 2009/0234359 A1 | 9/2009 | Onoue et al. |
| 2009/0248087 A1 | 10/2009 | Lewis |
| 2009/0281571 A1 | 11/2009 | Weaver et al. |
| 2009/0312801 A1 | 12/2009 | Lemoine et al. |
| 2010/0042161 A1 | 2/2010 | Worcel |
| 2010/0057127 A1 | 3/2010 | McGuire |
| 2010/0063505 A1 | 3/2010 | Frigg |
| 2010/0076496 A1 | 3/2010 | Fernandez |
| 2010/0198221 A1 | 8/2010 | Hearn |
| 2011/0160776 A1 | 6/2011 | Erickson et al. |
| 2012/0083846 A1 | 4/2012 | Wallenstein |
| 2012/0265203 A1 | 10/2012 | Angelucci |

FOREIGN PATENT DOCUMENTS

| | | |
|---|---|---|
| EP | 1637085 A2 | 3/2006 |
| FR | 2713473 A1 * | 6/1995 |
| FR | 2790198 A1 | 9/2000 |
| FR | 2792185 A1 | 10/2000 |
| FR | 2903880 A1 | 1/2008 |
| GB | 2305483 A | 4/1997 |
| GB | 2392096 A | 2/2004 |
| WO | WO-8803781 | 6/1988 |
| WO | WO-9306789 | 4/1993 |
| WO | WO-9722306 | 6/1997 |
| WO | WO-0078238 | 12/2000 |
| WO | WO-2005009487 | 2/2005 |
| WO | WO-2005053550 | 6/2005 |
| WO | WO-2005060845 | 7/2005 |
| WO | WO-2006072284 | 7/2006 |
| WO | WO-2008145902 | 12/2008 |
| WO | WO-2009105066 | 8/2009 |
| WO | WO-2009148697 | 12/2009 |

* cited by examiner

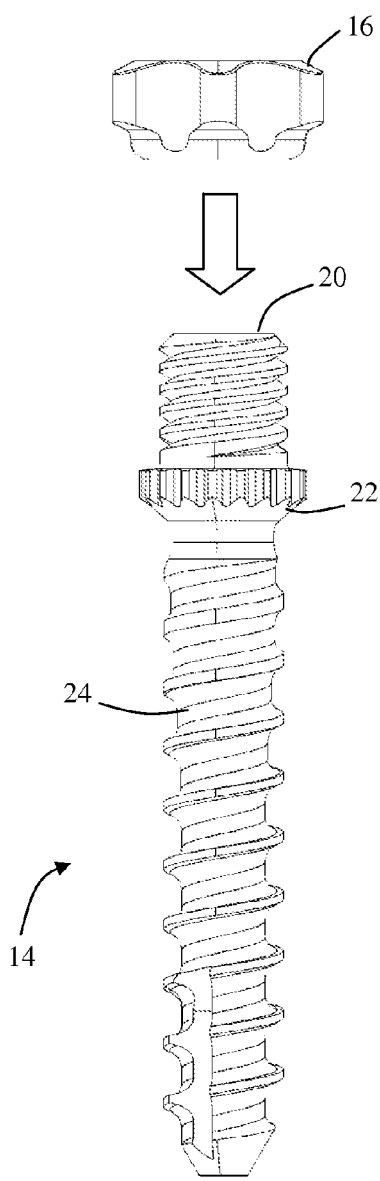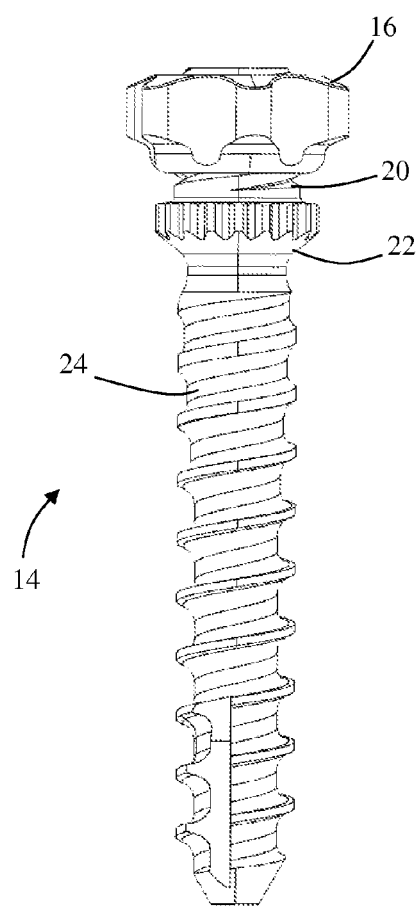
Fig. 15
Fig. 16

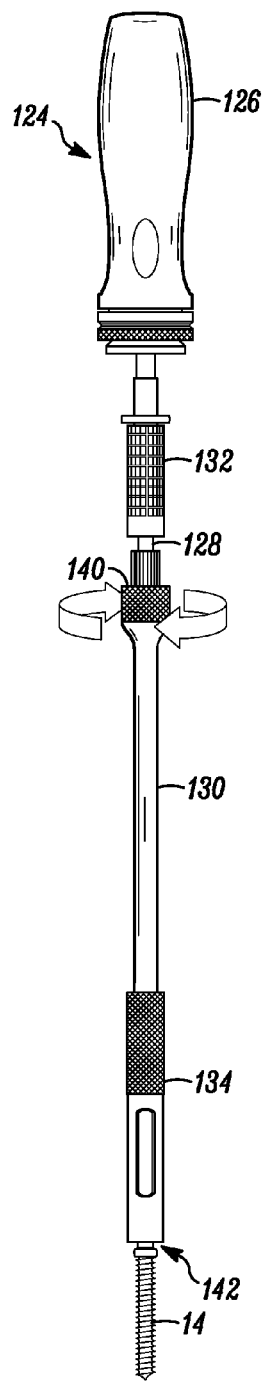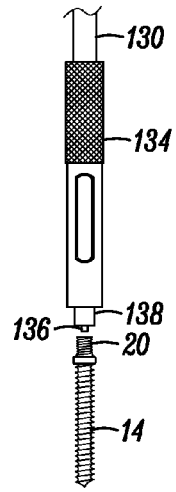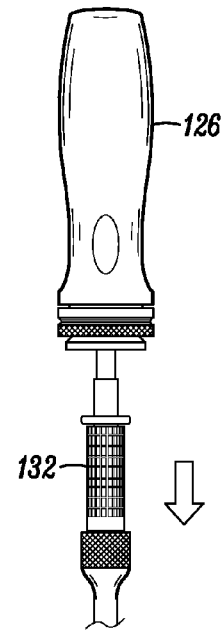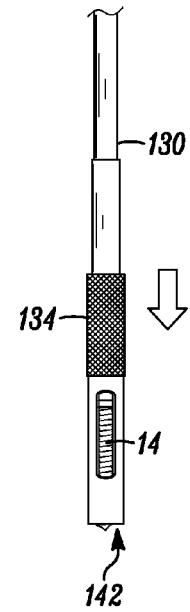
FIG. 25
FIG. 26
FIG. 27
FIG. 28

SURGICAL FIXATION SYSTEM AND RELATED METHODS

CROSS REFERENCE TO RELATED APPLICATIONS

The present application is a nonprovisional patent application claiming the benefit of priority under 35 U.S.C. §119(e) from U.S. Provisional Patent Application Ser. No. 61/025,702, filed on Feb. 1, 2008, the entire contents of which is hereby expressly incorporated by reference into this disclosure as if set forth fully herein. The present application also incorporates by reference the following documents into this disclosure in their entireties: U.S. patent application Ser. No. 10/967,668, filed on Oct. 18, 2004 and entitled "Surgical Access System and Related Methods;" and U.S. patent application Ser. No. 11/093,409 filed on Mar. 29, 2005 and entitled "Systems and Methods for Spinal Fusion."

BACKGROUND OF THE INVENTION

I. Field of the Invention

The present invention relates generally to spinal surgery and, more particularly, to systems and methods for repairing and/or reconstructing affected skeletal structures.

II. Discussion of the Prior Art

Each year millions of people suffer from back pain arising from defects in the intervertebral disc space. Commonly, surgical interventions directed at promoting fusion across the affected joint are employed to permanently provide long term pain relief to the patient. Typically, such fusion surgeries involve performing a partial or complete discectomy to prepare the disc space, and then implanting a natural or synthetic intervertebral fusion implant within the prepared disc space. Supplemental fixation, such as bone plates (anterior or posterior) or rod systems (posterior) may be further employed to provide stability across the affected joint while the body goes through the fusion process. Plate implants have been used for many years to aid in the promotion of fusion across affected vertebral disc spaces through stabilization of the joint. These spinal fixation plates are directed at complete immobilization of the affected joint while affording the optional benefit of restricting fusion inducing materials such as bone grafts within the joint. As a result of the fusion of adjacent vertebral bodies, the disc height between the vertebral bodies is restored, thereby reducing pain in the patient.

During a lateral access surgery performed through a minimally invasive operative corridor, it can be a challenge to obtain the angle or exposure necessary to properly implant an anterior or posterior supplemental fixation apparatus. Often, additional incisions must be made to accommodate placement of such fixation devices. The present invention is directed at overcoming, or at least improving upon, the disadvantages of the prior art.

SUMMARY OF THE INVENTION

The present application solves addresses this problem by providing a surgical fixation system including a base plate, a plurality of anchors, and a plurality of locking elements. The example shown and described herein is in the form of a base plate configured for a single-level spinal fusion, and as such the bone plate is sized and configured to span a single intervertebral space while achieving purchase within each of the vertebral bodies adjacent the single intervertebral space. However, the base plate may be provided in any number of sizes to accommodate multiple-level spinal fusions without departing from the scope of the present invention, depending upon the specific needs of the user.

The base plate is provided with a pair of fixation apertures configured to receive at least a portion of the anchors therethrough. The fixation apertures are provided by example as elongated slots, however, the fixation apertures may be provided with any shape suitable for receiving at least a portion of the anchors therethrough, including but not limited to circular or ovoid, without departing from the scope of the present invention. The fixation apertures are located within the base plate such that upon proper placement of the base plate within a surgical target site, one of the fixation apertures is positioned over a first bone segment (e.g. a first vertebral body), and the other fixation aperture is positioned over a second bone segment (e.g. a second vertebral body).

The anchors are shown and described herein by way of example only in the form of bone screws, however other forms of anchors are possible. The anchors include a head, intermediate region, and an elongated shaft. The head is configured to engage the locking element. When the surgical fixation system is fully assembled, the head and elongated shaft extend in opposite directions from the base plate. As such, the elongated shaft is able to provide purchase within a bony segment (e.g. vertebral body) while the head engages the locking element to secure the construct.

The base plate has a first end, a second end, first side, and second side. The base plate further includes a first surface and a second surface opposite the first surface. When properly positioned on a lateral aspect of a spinal column, second surface interfaces with the bone and thus is a vertebral contacting surface. Moreover, the first end represents the cephalad-most (or top) end of the base plate, the second end represents the caudal-most (or bottom) end of the base plate, the first side represents the anterior-most (or front) side of the base plate, and the second side represents the posterior-most (or back) side of the base plate. Within this disclosure, "first surface" and "second surface" may be used interchangeably with "top surface" and "bottom surface" to describe the same features of the base plate. Similarly, "first end," "second end," "first side," and "second side" may be used interchangeably with "top end," "bottom end," "front side," and "back side" to describe the same features of the base plate throughout this disclosure.

The fixation apertures are shown and described herein as being elongated slots. The purpose of the elongated slots is to allow for slight variable placement of the anchors within the vertebral bone. The interaction between the chocks on the anchors and the contoured periphery of the second recess of the base plate prevent the base plate from migrating relative to the anchors once the base plate is implanted. Each fixation aperture extends through the base plate from the top surface to the bottom surface. A first recess is formed within the top surface of the base plate around each fixation aperture. The first recess is shown by way of example of having a concavely sloped surface extending between the top surface to the mouth of the fixation aperture. The sloped surface interfaces with the lower exterior portion of the locking element so as to form a seat for the locking element and effectively prevent passage of the locking element through the fixation aperture. To accomplish this, the shape of the sloped surface corresponds directly with the shape of the lower exterior portion of the locking element.

A second recess is formed within the bottom surface of the base plate around each fixation aperture. By way of example only, the second recess includes a contoured periphery that is shown by way of example only as having a sunburst-shaped pattern. The contoured periphery is in the form of vertically-oriented chocks which interface and engage with the chocks of the anchors to help secure the base plate in place. As such, the contoured periphery has a shape that corresponds to the shape of the chocks of the anchors. In contrast to the sloped nature of the first recess, the second recess is formed in the bottom surface in a generally perpendicular fashion. This results in the formation of a shelf on the underside of the fixation aperture. The shelf functions to prevent the anchors from passing through the fixation apertures, and this prevents backout of the anchors once implanted.

The base plate further includes an insertion aperture including a threaded periphery for engaging with a threaded element of an insertion device. Surrounding the insertion aperture is a recess formed within the top surface of the base plate. The insertion aperture extends between the recess and the bottom surface. The recess is provided with a generally ovoid shape. The recess is configured to receive a portion of a distal end of an insertion instrument and thus the shape of the recess corresponds to the shape of the distal end of the insertion instrument. However, it is important to note that the ovoid shape of the recess provides an anti-torque feature to prevent rotation of the plate during the tightening of the locking elements. Moreover, the ovoid shape of the recess is significant in that it reduces the stress on the plate after implantation.

The top surface is generally planar. This feature helps to decrease the overall profile of the construct upon insertion into the spine. The bottom surface is generally concave in shape to provide a better fit with the natural curvature of the vertebral bodies. The combination of a generally planar top surface and a generally concave bottom surface results in a base plate having a first and second ends having a greater thickness than the middle portion of the plate.

The anchor includes a head at its proximal end, an intermediate region, and an elongated shaft extending distally from the intermediate region. The head has a generally cylindrical shape and extends generally perpendicularly in proximal direction from the top of the intermediate region. The head includes an exterior threadform configured to engage the locking element. The head further includes a recess for receiving a portion of an insertion instrument.

The intermediate region protrudes radially and generally perpendicularly from the anchor such that the intermediate region has an outer diameter that is greater than the outer diameters of both the head and elongated shaft. This prevents the anchor from passing though the insertion aperture of the base plate. The intermediate region includes a plurality of vertically-oriented chocks distributed in a radial gear-shaped pattern about the anchor. The chocks are configured to engage with the contoured periphery of the second recess of the base plate to prohibit migration of the base plate relative to the anchors once implanted. The intermediate region has a generally planar proximal-facing surface configured to flushly engage with the shelf of the second recess when the base plate is fully seated upon the anchors. The intermediate region further has a sloped distal-facing surface configured to contact the relevant bony structures (e.g. vertebral bodies).

The elongated shaft extends distally from the intermediate region. The shaft includes a threadform configured to provide purchase into bone. By way of example only, the threadform is provided as a single-lead threadform, however multiple threads may be used without departing from the scope of the present invention. The shaft further includes a notch to provide the anchor with a self-tapping feature. Furthermore, the anchor may be provided with a lumen extending therethrough such that the anchor is cannulated. The anchor has a major diameter defined by the outer diameter of the threadform.

The locking element is shown and described herein in the form of a lock nut, however other locking elements are possible without departing from the scope of the present invention. The locking element includes a central aperture, an upper exterior portion, and a lower exterior portion. The central aperture is sized and configured to receive the head of the anchor therein. To facilitate this engagement, the central aperture is provided with a threadform that complements the thread of the head. The upper exterior portion is configured to engage the distal end of an insertion device. The upper exterior portion has a generally sunburst shaped cross-section, with a plurality of radial protrusions separated by a plurality of recesses. The recesses serve as a location for engagement of the inserter. The locking element further includes a lower exterior portion extending below the upper exterior portion. The lower exterior portion has a generally convex curved shape to facilitate engagement with the first recess of the base plate.

To assemble the construct, the anchors are first provided and placed in a desired location. The base plate is then advanced over the anchors such that the chocks of the anchors are received within the second apertures of the bottom surface of the base plate. The chocks are aligned such that they engage the contoured periphery of the second apertures. At this point, the anchors are positioned such that a significant portion of the heads are protruding beyond the top surface of the base plate and a significant portion of the elongated shafts of the anchors are protruding beyond the bottom surface of the base plate. To lock the base plate and the anchors in place, the locking elements are advanced along the heads until they engage the base plate. As the locking element is advanced onto the head of the anchor (via the engagement between threads of the locking element and threads of the head), the lower exterior portion will be received into the first recess of the base plate. The lower exterior portion will interface with the sloped surface and exert a force on the base plate, essentially sandwiching the base plate between the anchor and the locking element. At this point the construct is fully assembled and locked in place.

The surgical fixation system of the present invention is assembled in situ during a surgical procedure. One such example is a spinal fusion surgery. The surgical fixation system disclosed herein is optimally used in a direct lateral surgical procedure, in which the spine is approached laterally at approximately a 90° angle relative to the patient's spine. The first step in such a procedure is to create an operative corridor through the patient's skin and underlying musculature to the surgical target site, for example a symptomatic intervertebral disc located between first and second adjacent vertebral bodies. The specific technique involved in performing this step is shown and describe in commonly owned and co-pending U.S. patent application Ser. No. 10/967,668, filed on Oct. 18, 2004 and entitled "Surgical Access System and Related Methods," the entire contents of which are hereby incorporated by reference into this disclosure as if set forth fully herein.

After establishment of the operative corridor to the surgical target site, the next step is to perform the necessary therapeutic technique to relieve the distress on the target disc space. For example, this may involve performing a partial or total discectomy—removing damaged or degenerative disc tissue from the intervertebral space and then inserting a spinal fusion implant such as a bone graft (e.g. allograft, autograft, or xenograft) or synthetic fusion cage (e.g. titanium and/or PEEK) into the space. One example of a synthetic spinal fusion implant that may be used is shown and described in commonly owned and co-pending U.S. patent application Ser. No. 11/093,409 filed on Mar. 29, 2005 and entitled "Systems and Methods for Spinal Fusion," the entire contents of which are hereby incorporated by reference into this disclosure as if set forth fully herein. These spinal fusion implants (natural or synthetic) may be used with or without additional fusion inducing materials, such as an orthopedic matrix containing for example (including but not limited to) calcium hydroxyapatite, bone morphogenic protein (BMP), demineralized bone matrix, collagen bone graft matrix (e.g. Formagraft®) and stem cell material (e.g. Osteocel®), or other fusion-promoting substances placed within the spaces of the implant, while the implant is advanced into the intervertebral space.

After addressing the distressed disc space, the next step is to add supplemental fixation, if desired. In this case the surgical fixation system of the present invention is implanted through the operative corridor within the surgical target site to help with the fusion process. The first step in implanting the surgical fixation system is to implant the anchors within the first and second vertebral bodies. A variety of instruments may be provided to assist in the implantation of the surgical fixation system of the present invention. For example, a guide member having insertion apertures and a plurality of guide barrels may be provided for aiding in the proper placement of the anchors within the vertebral bodies. Once the guide member is properly seated within the surgical target site, the surgeon proceeds with pilot hole formation to prepare the vertebral bodies for receiving the anchors. Formation of the pilot hole may be accomplished via a number of different techniques and instruments depending upon the surgeon's preference, including but not limited to using drills, taps, awls, etc. to create a pilot hole that is preferably undersized by 1 mm relative to the anchors to be used in order to maximize the purchase of the anchors within the bone.

Upon formation of the pilot hole, a driver is used to insert the anchors through the guide barrels, apertures, and into the bone. Once both anchors are properly implanted within the vertebral bodies the base plate is implanted within the surgical target site. Upon seating of the base plate on the anchors, the locking elements are applied to secure the base plate in place and complete assembly of the surgical fixation system. A locking element inserter may be provided to further this purpose.

At this stage, the surgical fixation system is fully assembled in situ and implanted into a surgical target site. The procedure being completed, the operative corridor is closed and the incision is stitched up.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 15 is a front plan view of the anchor of FIG. 8 and lock nut of FIG. 11 prior of engagement of the locking element to the anchor;

FIG. 16 is a front plan view of the anchor and locking element of FIG. 15 in an assembled state;

FIG. 25 is a front plan view of a screw inserter for use with the surgical fixation system of FIG. 1 according to a further embodiment of the present invention;

FIG. 26 is a front plan view of the distal region of the screw inserter of FIG. 25 prior to engagement with a bone screw;

FIG. 27 is a front plan view of the proximal region of the screw inserter of FIG. 25;

FIG. 28 is a front plan view of the distal region of the screw inserter of FIG. 25 after engagement with a bone screw and prior to insertion into the body;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical fixation system and related methods disclosed herein boasts a variety of inventive features and components that warrant patent protection, both individually and in combination.

Figure 1:
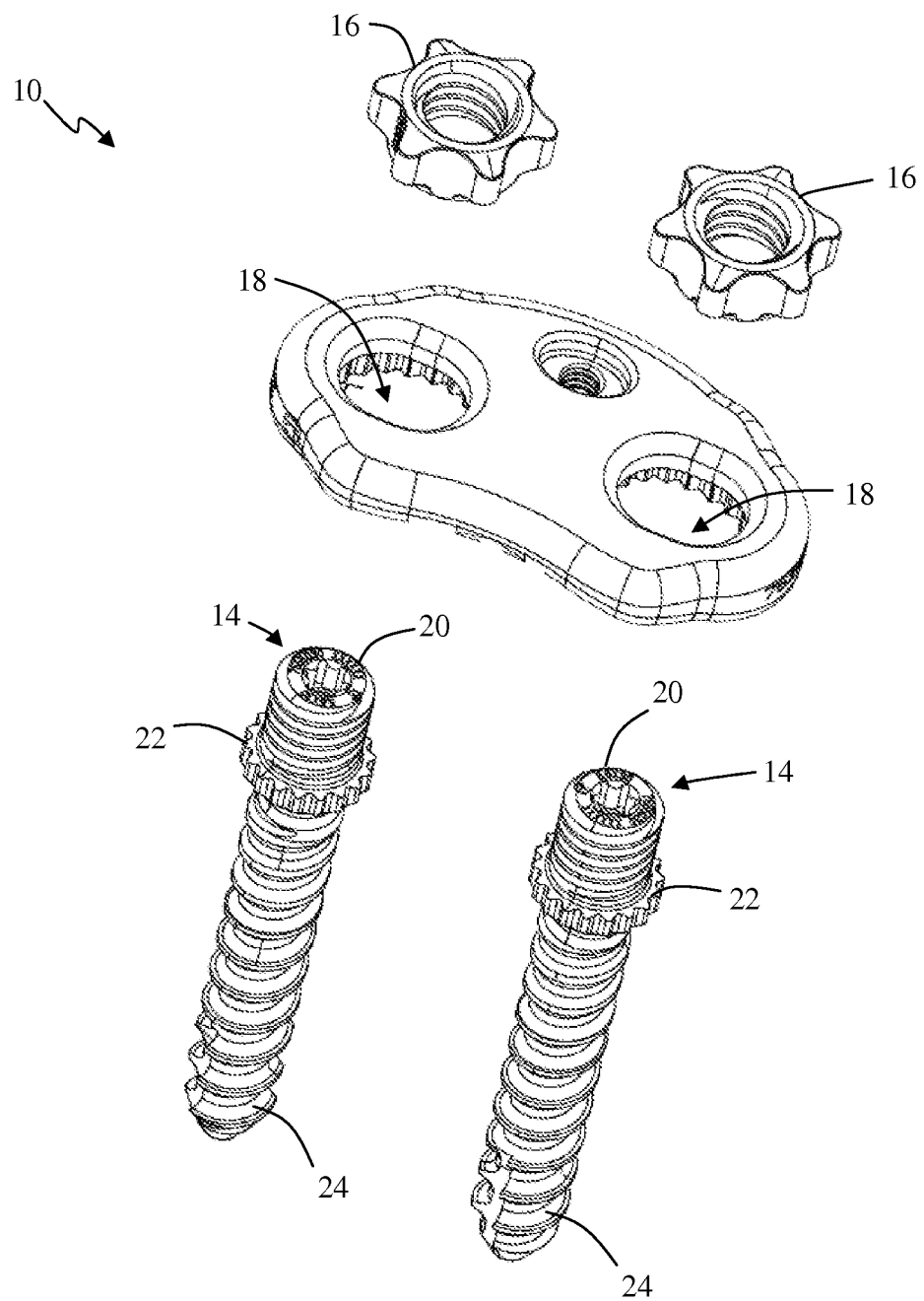
FIG. 1 is an exploded perspective view of one example of surgical fixation system according to one embodiment of the present invention.
Figure 2:
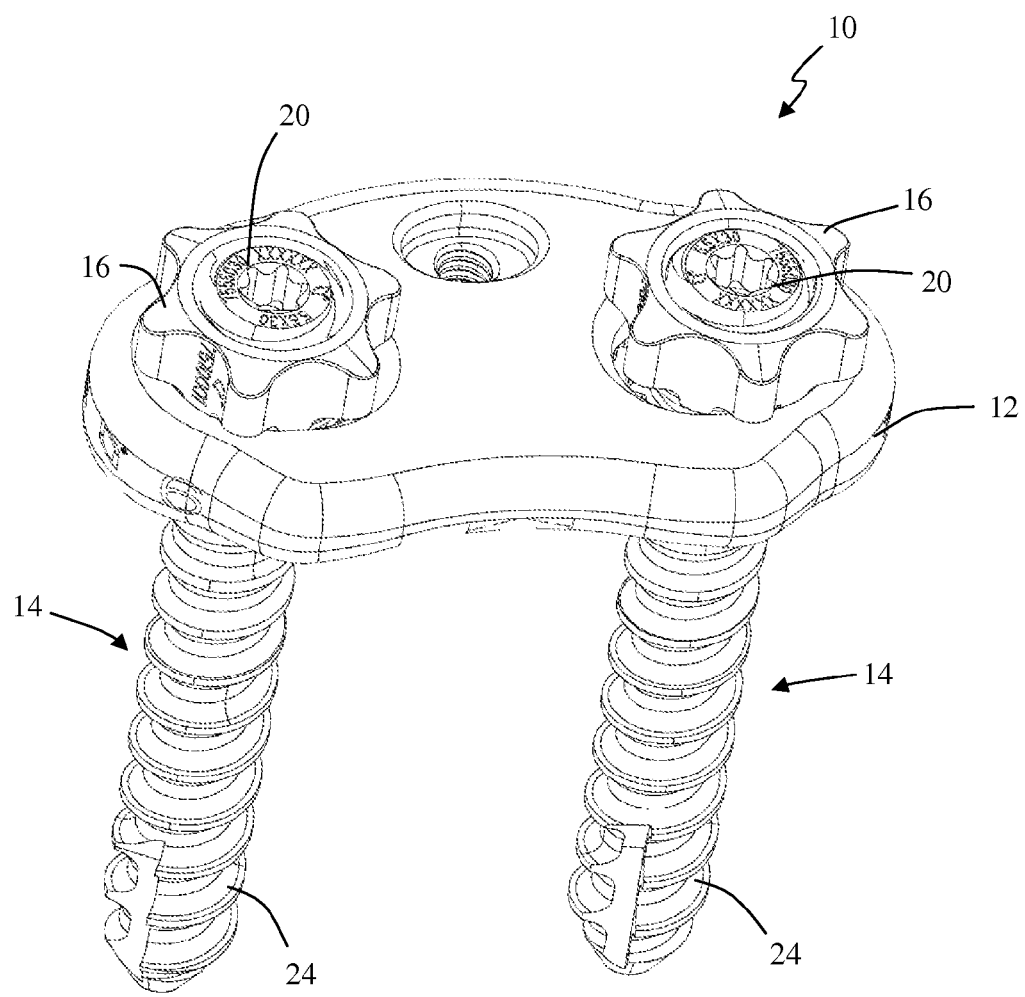
FIG. 2 is a top perspective view of the surgical fixation system of FIG. 1 in an assembled state.
Figure 3:
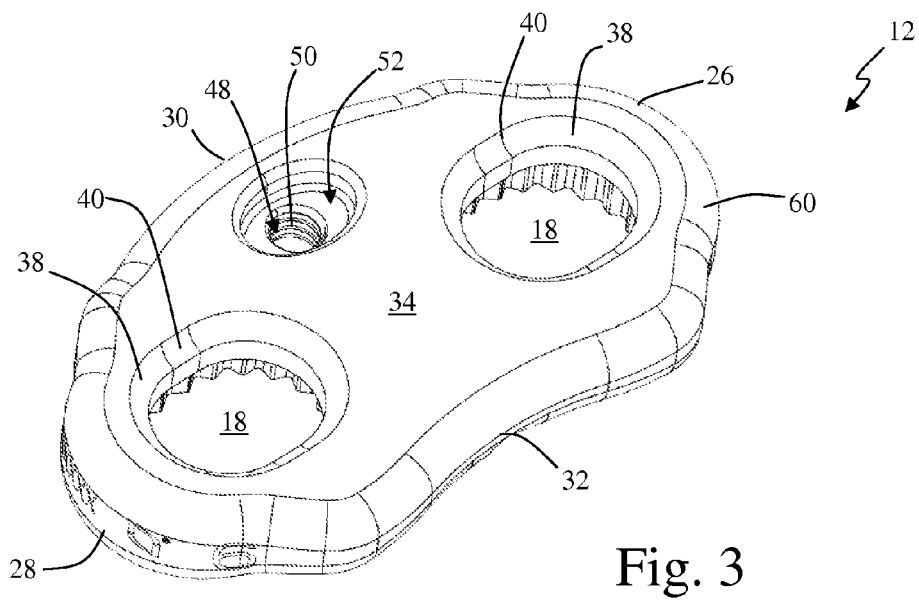
FIG. 3 is a top perspective view of a bone plate forming part of the surgical fixation system of FIG. 1.

FIGS. 1-2 illustrate an example of a surgical fixation system 10 according to one embodiment of the present invention. The surgical fixation system 10 includes a base plate 12, a plurality of anchors 14, and a plurality of locking elements 16. The example shown and described herein is in the form of a base plate 12 configured for a single-level spinal fusion, and as such the bone plate is sized and configured to span a single intervertebral space while achieving purchase within each of the vertebral bodies adjacent the single intervertebral space. However, the base plate 12 may be provided in any number of sizes to accommodate multiple-level spinal fusions without departing from the scope of the present invention, depending upon the specific needs of the user.

The base plate 12 is provided with a pair of fixation apertures 18 configured to receive at least a portion of the anchors 14 therethrough. The fixation apertures 18 are provided by example as elongated slots, however, the fixation apertures 18 may be provided with any shape suitable for receiving at least a portion of the anchors 14 therethrough, including but not limited to circular, ovoid, or polygonal (e.g. rectangular, triangular, square, etc.), without departing from the scope of the present invention. As will be explained in further detail below, the fixation apertures 18 are located within the base plate 12 such that upon proper placement of the base plate 12 within a surgical target site, one of the fixation apertures 18 is positioned over a first bone segment (e.g. a first vertebral body), and the other fixation aperture 18 is positioned over a second bone segment (e.g. a second vertebral body).

The anchors 14 are shown and described herein by way of example only in the form of bone screws, however other forms of anchors are possible. The anchors 14 include a head 20, intermediate region 22, and an elongated shaft 24. As will be explained in further detail below, the head 20 is configured to engage the locking element 16. As shown in FIG. 2, when the surgical fixation system 10 is fully assembled, the head 20 and elongated shaft 24 extend in opposite directions from the base plate 12. As such, the elongated shaft 24 is able to provide purchase within a bony segment (e.g. vertebral body) while the head 20 engages the locking element 16 to secure the construct.

Referring to FIGS. 3-7, the bone plate will now be described in further detail. The base plate 12 has a first end 26, a second end 28, first side 30, and second side 32. The base plate 12 further includes a first surface 34 and a second surface 36 opposite the first surface 34. When properly positioned on a lateral aspect of a spinal column, second surface 36 interfaces with the bone and thus is a vertebral contacting surface. Moreover, the first end 26 represents the cephalad-most (or top) end of the base plate 12, the second end 28 represents the caudal-most (or bottom) end of the base plate 12, the first side 30 represents the anterior-most (or front) side of the base plate 12, and the second side 32 represents the posterior-most (or back) side of the base plate 12. Within this disclosure, "first surface 34" and "second surface 36" may be used interchangeably with "top surface 34" and "bottom surface 36" to describe the same features of the base plate 12. Similarly, "first end 26," "second end 28," "first side 30," and "second side 32" may be used interchangeably with "top end 26," "bottom end 28," "front side 30," and "back side 32" to describe the same features of the base plate 12 throughout this disclosure.

The base plate 12 may be provided in any shape suitable for spanning at least one intervertebral disc space without departing from the scope of the present invention. In the example provided, the base plate 12 has a general crescent shape, however straight lines are possible. More specifically, the first side 30 has a generally convex curvature as it extends between the first and second ends 26, 28. Similarly, the second side 32 has a generally concave curvature as it extends between the first and second ends 26, 28. This curvature may perform a variety of functions. First, the shape of the implant may help to ensure proper positioning the base plate 12 by the user. For example, the front side 30 has a generally convex curvature so as to mimic the lordotic curvature of the lumbar spine and give the user a visual similarity between the shape of the implant and the shape of the spine. Second, the concave back side 32 allows for less material to be used in constructing the implant, leading to a lower profile and less expensive construct. Although shown as having one convex side and one concave side, the base plate 12 may be provided with any combination of curved or straight sides without departing from the scope of the present invention.

Figure 36:
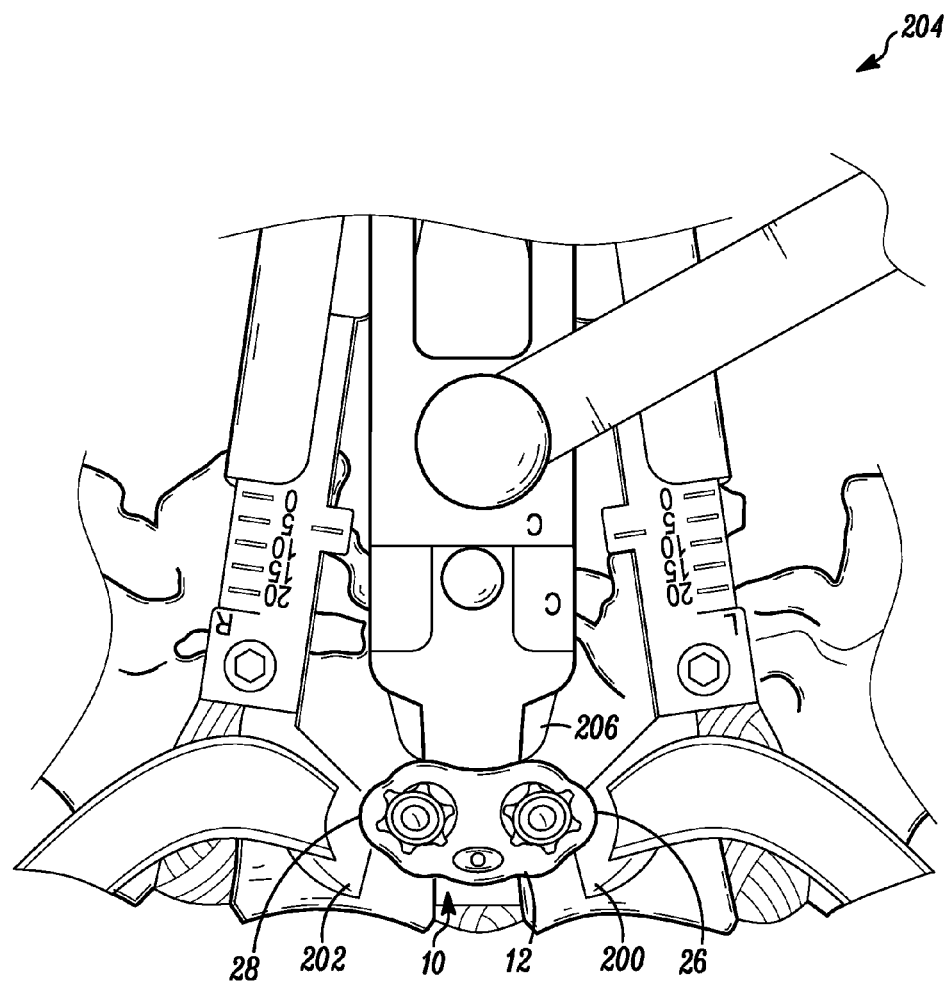
FIG. 36 is a top view of the surgical fixation system of FIG. 1 fully implanted onto a spinal column.

The first and second ends 26, 28 are shown by way of example only as being generally rounded. It is important to note that the overall shape of the base plate 12 is not a smooth kidney bean shape. More particularly, the first and second ends 26, 28 essentially form curved projections, or scallops extending in a cephalad or caudal direction. The scalloped shape of the first and second ends 26, 28 is significant in that the first and second ends 26, 28 each have a radius of curvature that is approximately equal to the radius of curvature of the retractor blades 20, 202 used to establish the operative corridor (FIG. 36). This is significant for a number of reasons. Most importantly, having radii of curvature of the first and second ends 26, 28 of the base plate 12 and the retractor blades 200, 202 of the surgical retraction system 204 enables the base plate 12 to be smoothly advanced along the operative corridor toward the surgical target site. This is a significant advantage when dealing with a minimally invasive operative corridor in terms of operative time savings and avoiding disruption of the operative corridor. Furthermore, having less plate material around the first and second ends 26, 28 enable for better visibility on the part of the surgeon when determining if placement of the plate was proper.

The fixation apertures 18 are shown and described herein as being elongated slots. The purpose of the elongated slots is to allow for slight variable placement of the anchors 14 within the vertebral bone. The interaction between the chocks 68 on the anchors 14 (FIG. 8) and the contoured periphery 44 of the second recess 42 of the base plate 12 (described below) prevent the base plate 12 from migrating relative to the anchors 14 once the base plate 12 is implanted. Each fixation aperture 18 extends through the base plate 12 from the top surface 34 to the bottom surface 36. As shown most clearly in FIGS. 3 and 5, a first recess 38 is formed within the top surface 34 of the base plate 12 around each fixation aperture 18. The first recess 38 is shown by way of example of having a concavely sloped surface 40 extending between the top surface 34 to the mouth of the fixation aperture 18. The sloped surface 40 interfaces with the lower exterior portion 84 (FIG. 13) of the locking element 16 so as to form a seat for the locking element 16 and effectively prevent passage of the locking element 16 through the fixation aperture 18. To accomplish this, the shape of the sloped surface 40 corresponds directly with the shape of the lower exterior portion 84 of the locking element 16. Thus, the sloped surface 40 may have other shapes (for example generally planar) depending upon the shape of the lower exterior portion 84 of the locking element 16. The locking element 16 is described in further detail below with reference to FIGS. 11-14.

Figure 4:
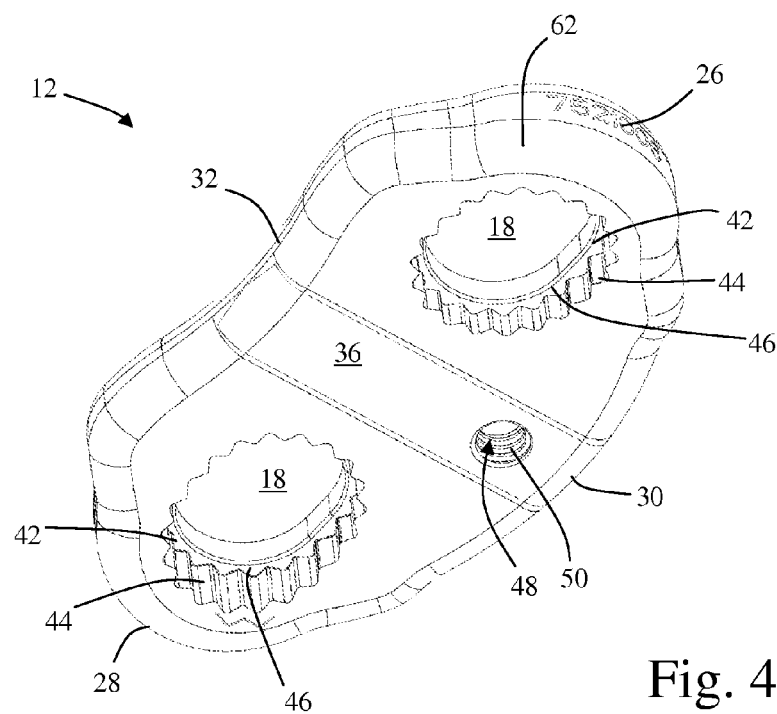
FIG. 4 is a bottom perspective view of the bone plate of FIG. 3.
Figure 5:
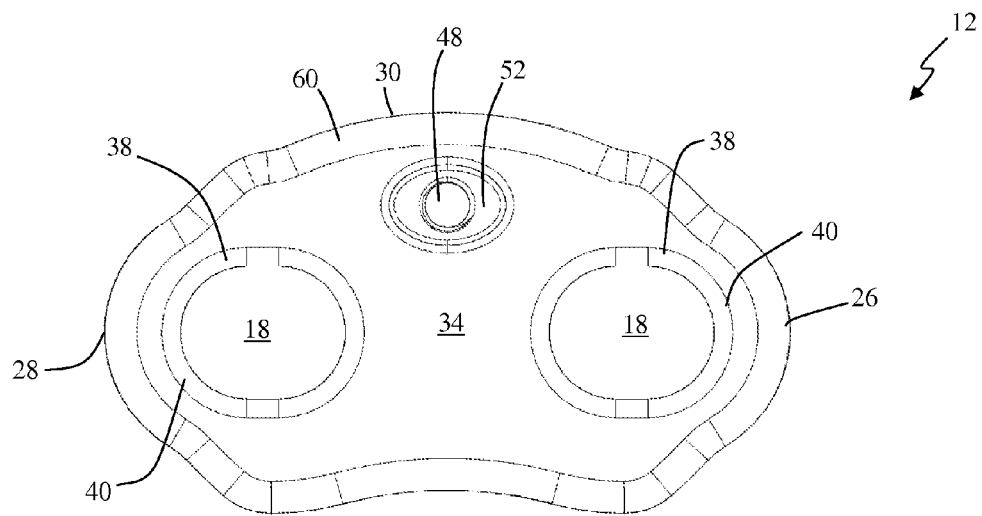
FIG. 5 is a top plan view of the bone plate of FIG. 3.
Figure 6:
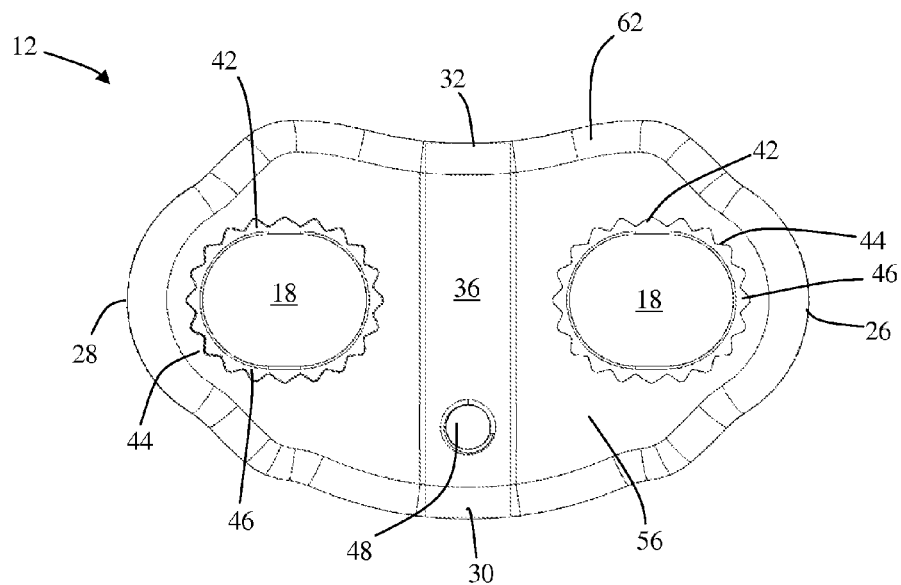
FIG. 6 is a bottom plan view of the bone plate of FIG. 3.

As shown most clearly in FIGS. 4 and 6, a second recess 42 is formed within the bottom surface 36 of the base plate 12 around each fixation aperture 18. By way of example only, the second recess 42 includes a contoured periphery 44 that is shown by way of example only as having a sunburst-shaped pattern. The contoured periphery 44 is in the form of vertically-oriented chocks which interface and engage with the chocks 68 of the anchors 14 to help secure the base plate 12 in place. As such, the contoured periphery 44 has a shape that corresponds to the shape of the chocks 68 of the anchors 14. In contrast to the sloped nature of the first recess 38, the second recess 44 is formed in the bottom surface 36 in a generally perpendicular fashion. This results in the formation of a shelf 46 on the underside of the fixation aperture 18. The shelf 46 functions to prevent the anchors 14 from passing through the fixation apertures 18, and this prevents backout of the anchors 14 once implanted.

Referring again to FIG. 3, the base plate 12 further includes an insertion aperture 48 including a threaded periphery 50 for engaging with a threaded element of an insertion device (not shown). Surrounding the insertion aperture 48 is a recess 52 formed within the top surface 34 of the base plate 12. The insertion aperture 48 extends between the recess 52 and the bottom surface 36. As shown most clearly in FIGS. 3 and 5, the recess 52 is provided with a generally ovoid shape. The recess 52 is configured to receive a portion of a distal end of an insertion instrument (FIG. 35) and thus the shape of the recess 52 corresponds to the shape of the distal end of the insertion instrument. However, it is important to note that the ovoid shape of the recess 52 provides an anti-torque feature to prevent rotation of the plate during the tightening of the locking elements 16. Moreover, the ovoid shape of the recess 52 is significant in that it reduces the stress on the plate after implantation.

Figure 7:
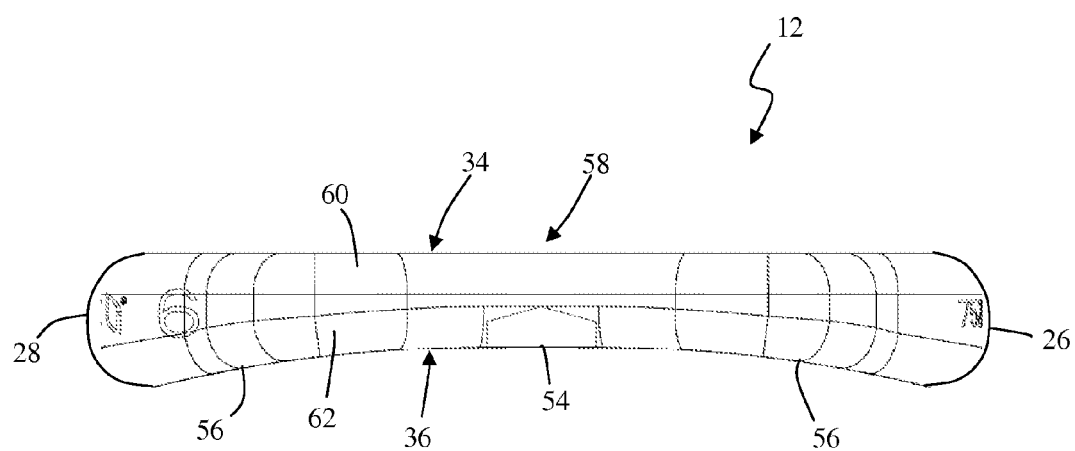
FIG. 7 is a front plan view of the bone plate of FIG. 3.
Figure 35:
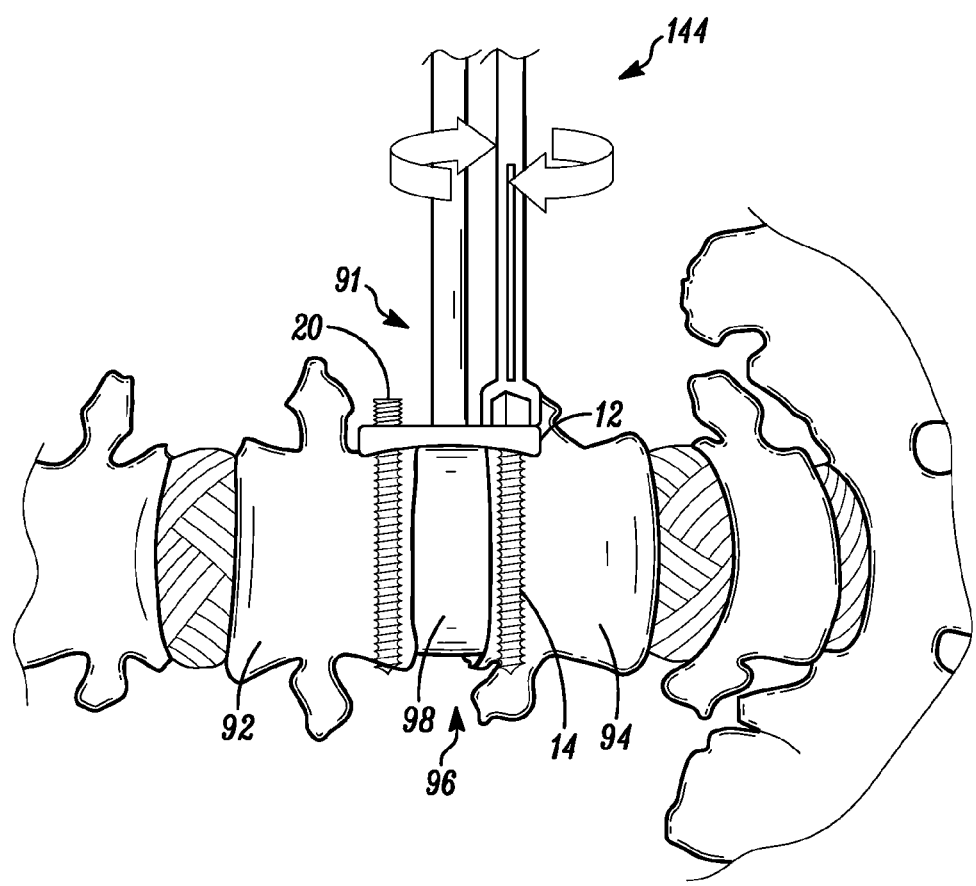
FIG. 35 is a side plan view of the locking element of FIG. 12 being inserted onto an implanted bone screw and bone plate combination.

As shown by way of example in FIG. 7, the top surface 34 is generally planar. This feature helps to decrease the overall profile of the construct upon insertion into the spine. The bottom surface 36 is generally concave in shape to provide a better fit with the natural curvature of the vertebral bodies (FIG. 35, for example). The bottom surface 36 may be provided with a continuous curve, or as shown by way of example only may have a generally planar middle portion 54 flanked on either side by a concavely curved portion 56. In any event, the combination of a generally planar top surface 34 and generally concave bottom surface 36 results in a base plate 12 having a first and second ends 26, 28 having a greater thickness than the middle portion 58 of the plate.

Referring again to FIGS. 3-7, the base plate 12 has generally rounded (e.g. convexly sloped) top and bottom peripheral surfaces 60, 62. This functions to remove potentially sharp edges from the construct in order to make it more environmentally friendly to the body.

Figures 8, 9:
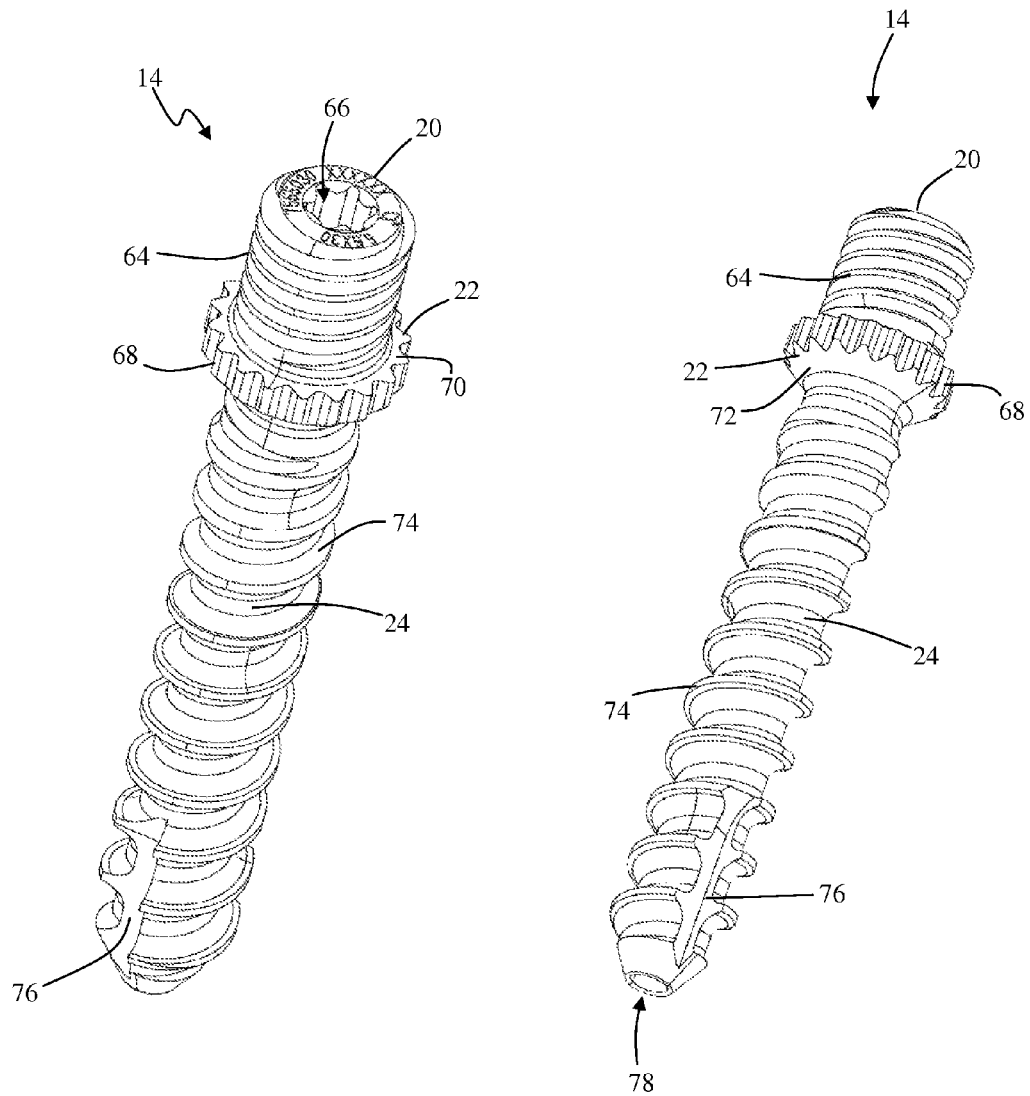
FIGS. 8 and 9 are perspective views of an anchor forming part of the surgical fixation system of FIG. 1.
Figure 10:
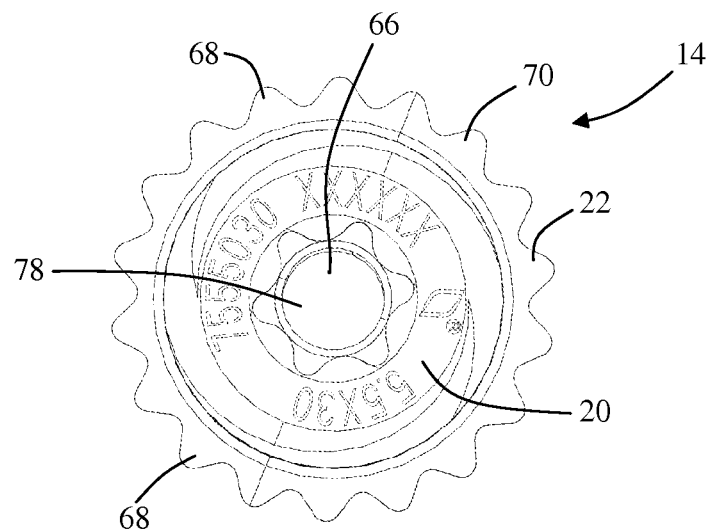
FIG. 10 is a top plan view of the anchor of FIG. 8.
Figure 11:
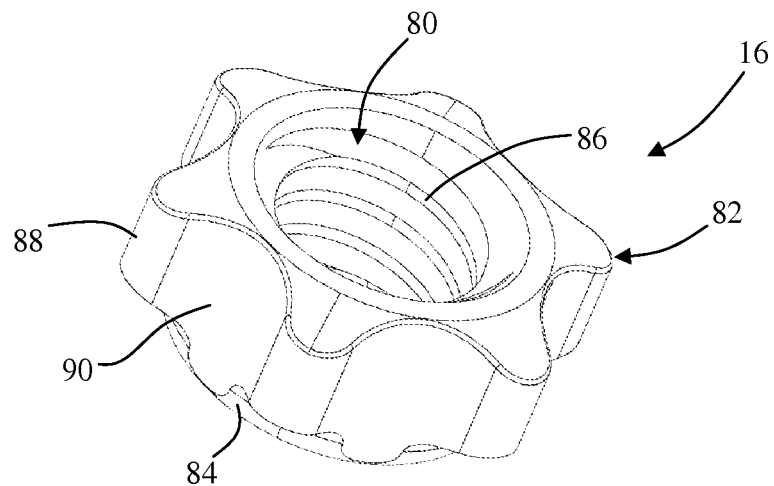
FIGS. 11 and 12 are perspective views of a locking element forming part of the surgical fixation system of FIG. 1.
Figure 12:
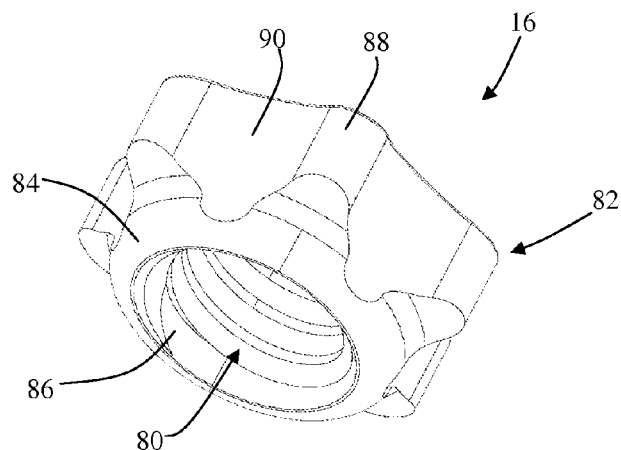

FIGS. 8-10 illustrate an example of an anchor 14 forming part of the surgical fixation system 10 described above. The anchor 14 includes a head 20 at its proximal end, an intermediate region 22, and an elongated shaft 24 extending distally from the intermediate region 22. The head 20 has a generally cylindrical shape and extends generally perpendicularly in proximal direction from the top of the intermediate region 22. The head 20 includes an exterior threadform 64 configured to engage the locking element 16. The head 20 further includes a recess 66 for receiving a portion of an insertion instrument (e.g. driver 124 of FIGS. 25-28). The recess 66 may have any shape that corresponds to the shape of the distal tip of the driver.

The intermediate region 22 protrudes radially and generally perpendicularly from the anchor 14 such that the intermediate region 22 has an outer diameter that is greater than the outer diameters of both the head 20 and elongated shaft 24. As will be seen, this prevents the anchor 14 from passing though the insertion aperture 18 of the base plate 12. The intermediate region 22 includes a plurality of vertically-oriented chocks 68 distributed in a radial gear-shaped pattern about the anchor 14. The chocks 68 are configured to engage with the contoured periphery 44 of the second recess 42 of the base plate 12 to prohibit migration of the base plate 12 relative to the anchors 14 once implanted. The intermediate region 22 has a generally planar proximal-facing surface 70 configured to flushly engage with the shelf 46 of the second recess 42 when the base plate 12 is fully seated upon the anchors 14, as will be described below. The intermediate region 22 further has a sloped distal-facing surface 72 configured to contact the relevant bony structures (e.g. vertebral bodies). The sloped distal-facing surface 72 may have any cross-sectional shape desired by the user, including but not limited to concave, convex, and/or generally planar.

The elongated shaft 24 extends distally from the intermediate region 22. The shaft 24 includes a threadform 74 configured to provide purchase into bone. By way of example only, the threadform 74 is provided as a single-lead threadform, however multiple threads may be used without departing from the scope of the present invention. The shaft 24 further includes a notch 76 to provide the anchor 14 with a self-tapping feature. Furthermore, the anchor 14 may be provided with a lumen 78 extending therethrough such that the anchor 14 is cannulated. The anchor 14 has a major diameter defined by the outer diameter of the threadform 74.

Figure 13:
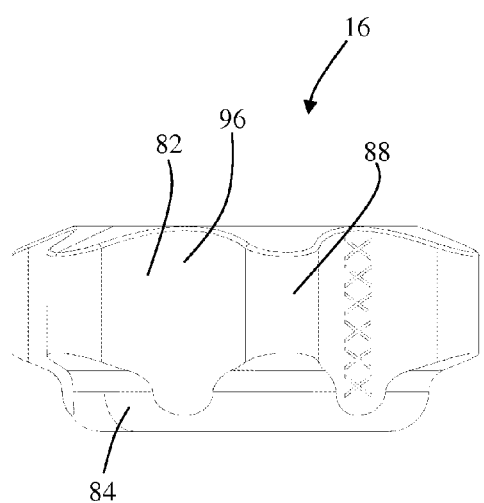
FIGS. 13 and 14 are side plan and bottom plan views, respectively, of the locking element of FIG. 11.
Figure 14:
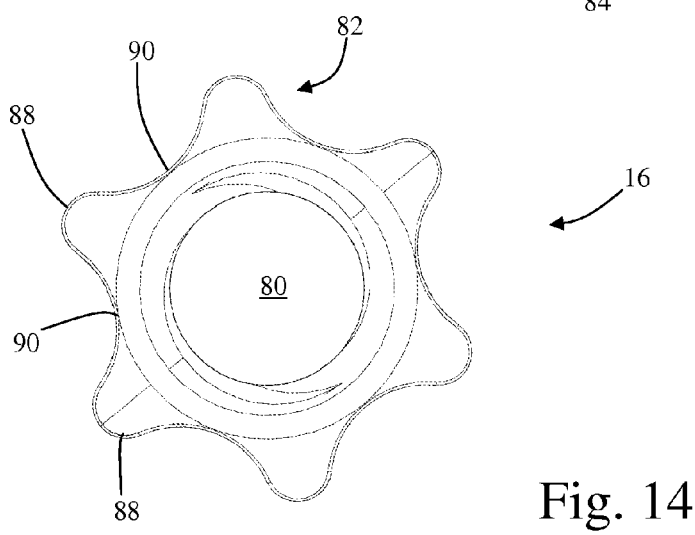
Figure 17:
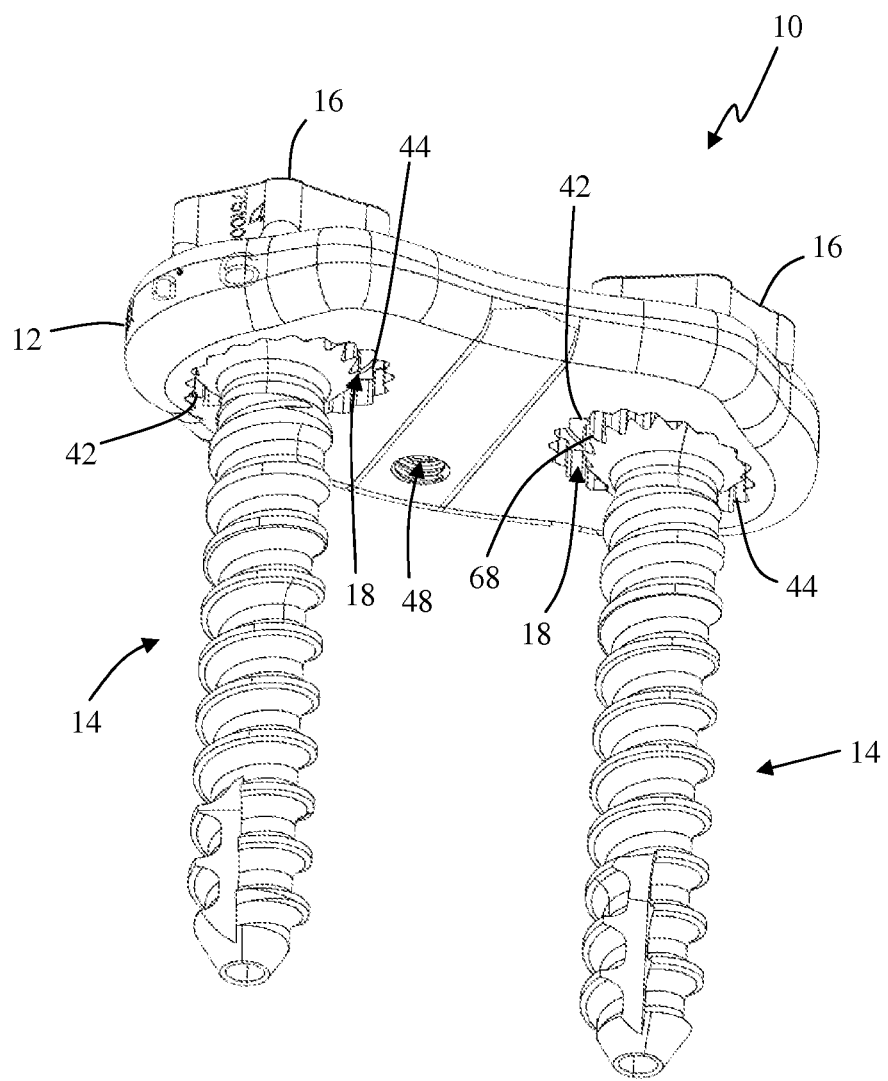
FIG. 17 is a bottom perspective view of the underside of the assembled surgical fixation system of FIG. 2.
Figure 18:
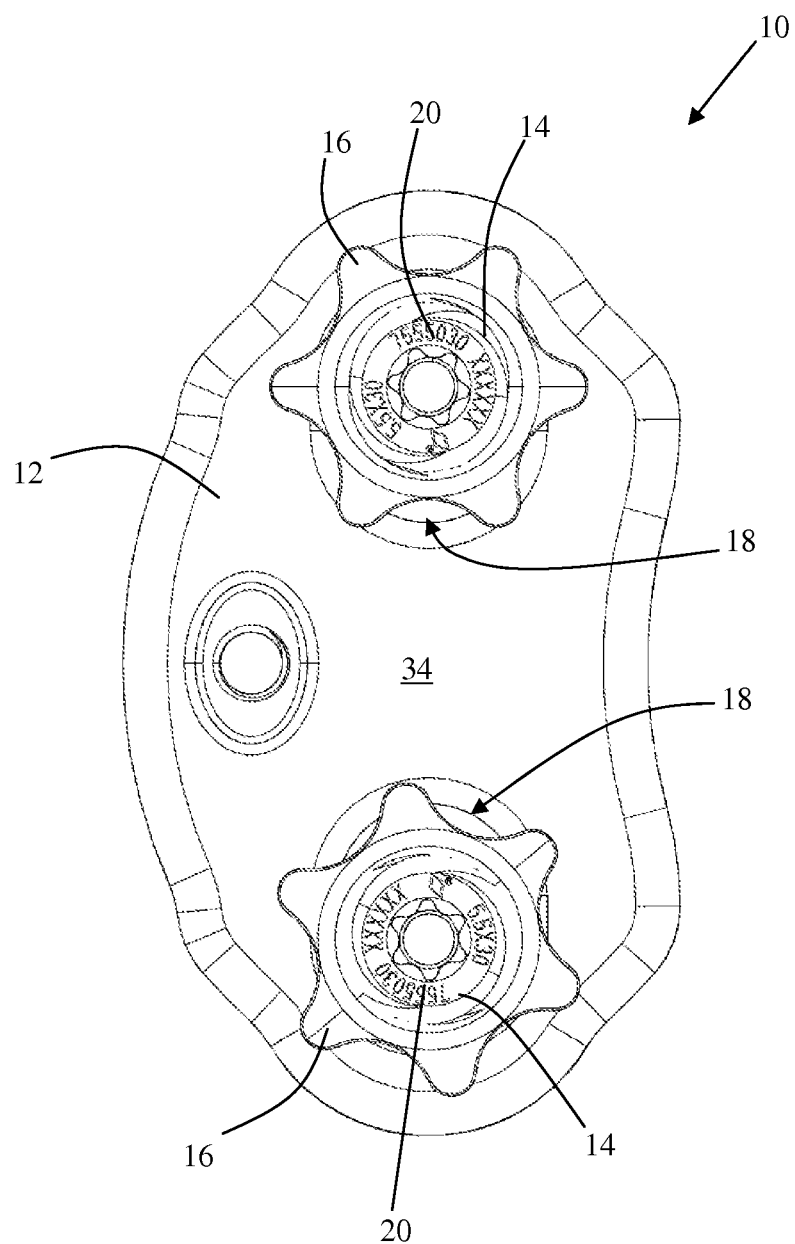
FIG. 18 is a top plan view of the assembled surgical fixation system of FIG. 2.
Figure 19:
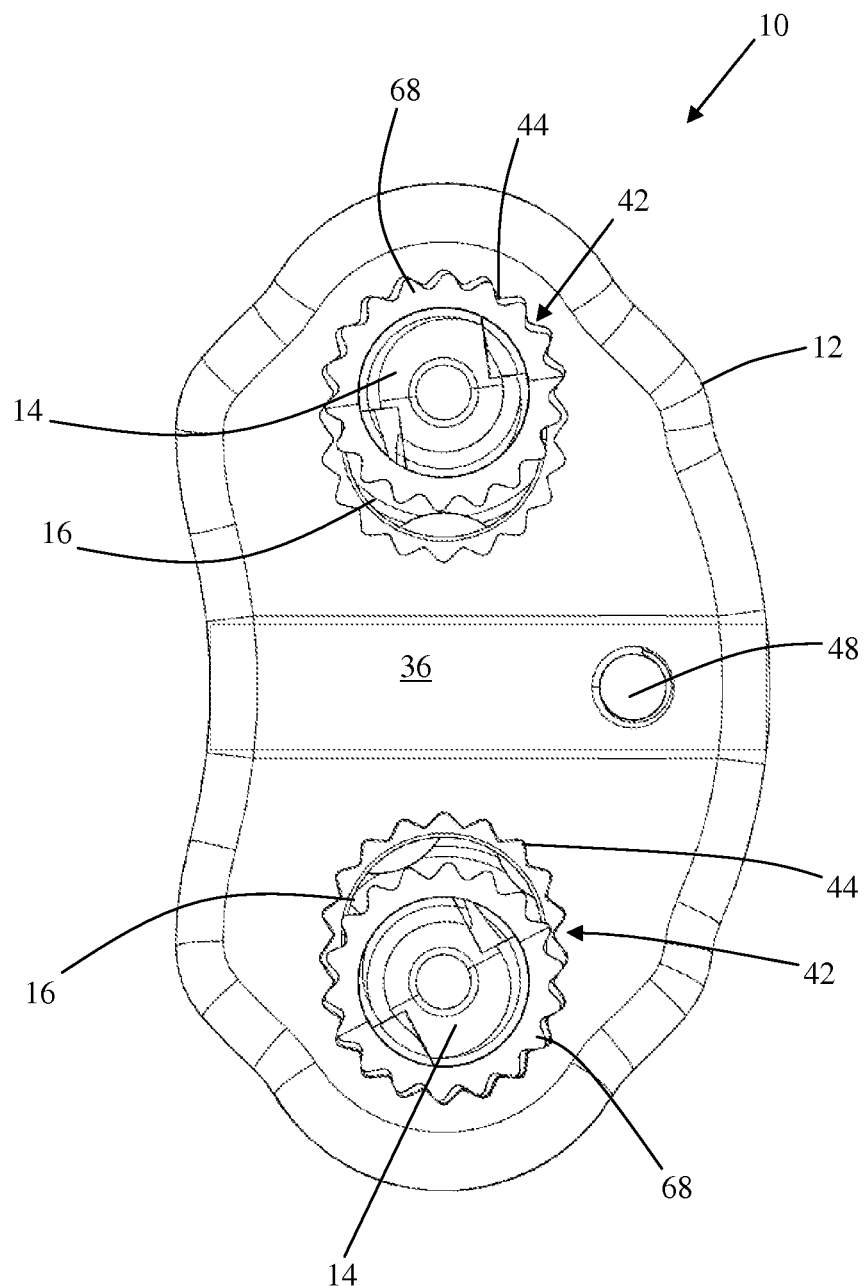
FIG. 19 is a bottom plan view of the assembled surgical fixation system of FIG. 2.
Figure 34:
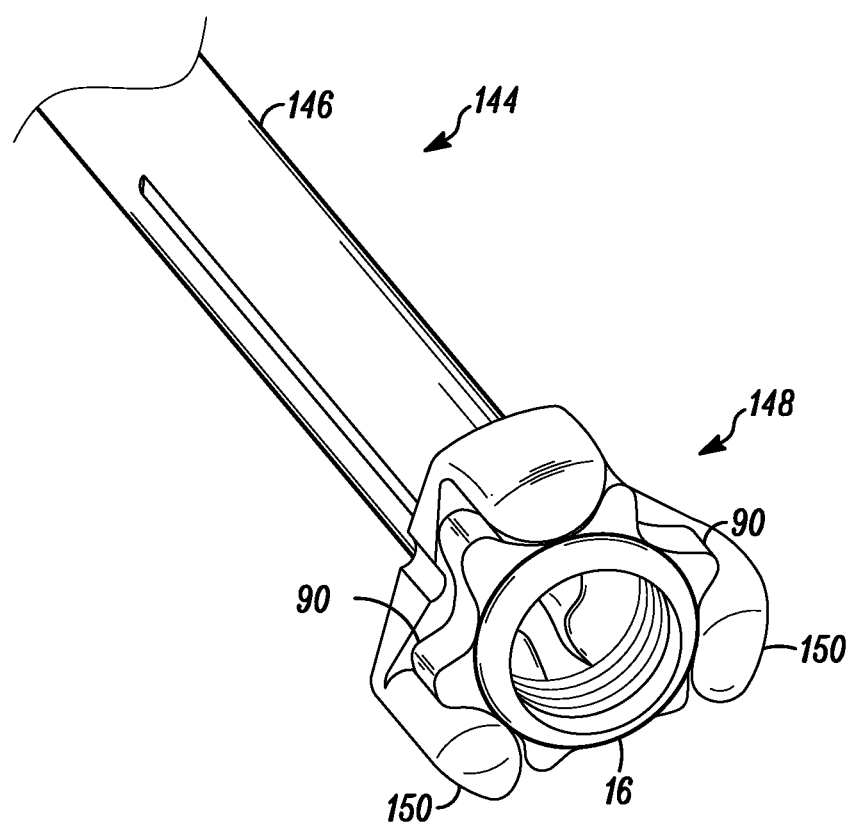
FIG. 34 is a perspective view of a distal end of a locking element inserter engaged to the locking element of FIG. 12.

FIGS. 11-14 illustrate an example of a locking element 16 forming part of the surgical fixation system 10 according to one embodiment of the present invention. By way of example only, the locking element 16 is shown and described herein in the form of a lock nut, however other locking elements are possible without departing from the scope of the present invention. The locking element 16 includes a central aperture 80, an upper exterior portion 82, and a lower exterior portion 84. The central aperture 80 is sized and configured to receive the head 20 of the anchor 14 therein. To facilitate this engagement, the central aperture 80 is provided with a threadform 86 that complements the thread 64 of the head 20. The upper exterior portion 84 is configured to engage the distal end of an insertion device (e.g. inserter 144 of FIG. 34). As best seen in FIG. 14, the upper exterior portion 84 has a generally sunburst shaped cross-section, with a plurality of radial protrusions 88 separated by a plurality of recesses 90. As seen in FIG. 34, the recesses 90 serve as a location for engagement of the inserter 144. Referring again to FIGS. 11-14, locking element 16 further includes a lower exterior portion 84 extending below the upper exterior portion 82. The lower exterior portion 84 has a generally convex curved shape (as best seen in FIG. 13) to facilitate engagement with the first recess 38 of the base plate 12.

FIGS. 15 and 16 illustrate the engagement of the locking element 16 with the anchor 14. To achieve this, the locking element 16 is advanced onto the head 20 of the anchor 14. The thread 86 of the locking element 16 cooperates with the thread 64 of the head 20 to create a threaded engagement. The locking element 16 may then be rotated in a clockwise direction to advance the locking element 16 onto the head 20 of the anchor 14. Rotation in a counterclockwise direction would cause the locking element 16 to retreat up the head 20, allowing for disengagement and removal if necessary.

FIGS. 17-21 illustrate the surgical fixation system 10 described above as an assembled construct. To assemble the construct, the anchors 14 are first provided and placed in a desired location. The base plate 12 is then advanced over the anchors 14 such that the chocks 68 of the anchors 14 are received within the second apertures 42 of the bottom surface 36 of the base plate 12. The chocks 68 are aligned such that they engage the contoured periphery 44 of the second apertures 42. At this point, the anchors 14 are positioned such that a significant portion of the heads 20 are protruding beyond the top surface 34 of the base plate 12 and a significant portion of the elongated shafts 24 of the anchors 14 are protruding beyond the bottom surface 36 of the base plate 12. To lock the base plate 12 and the anchors 14 in place, the locking elements 16 are advanced along the heads 20 until they engage the base plate 12. As the locking element 16 is advanced onto the head 20 of the anchor 14 (via the engagement between threads 86 of the locking element 16 and threads 64 of the head 20), the lower exterior portion 84 will be received into the first recess 38 of the base plate 12. The lower exterior portion 84 will interface with the sloped surface 40 and exert a force on the base plate 12, essentially sandwiching the base plate 12 between the anchor 14 and the locking element 16. At this point the construct is fully assembled and locked in place.

Figure 20:
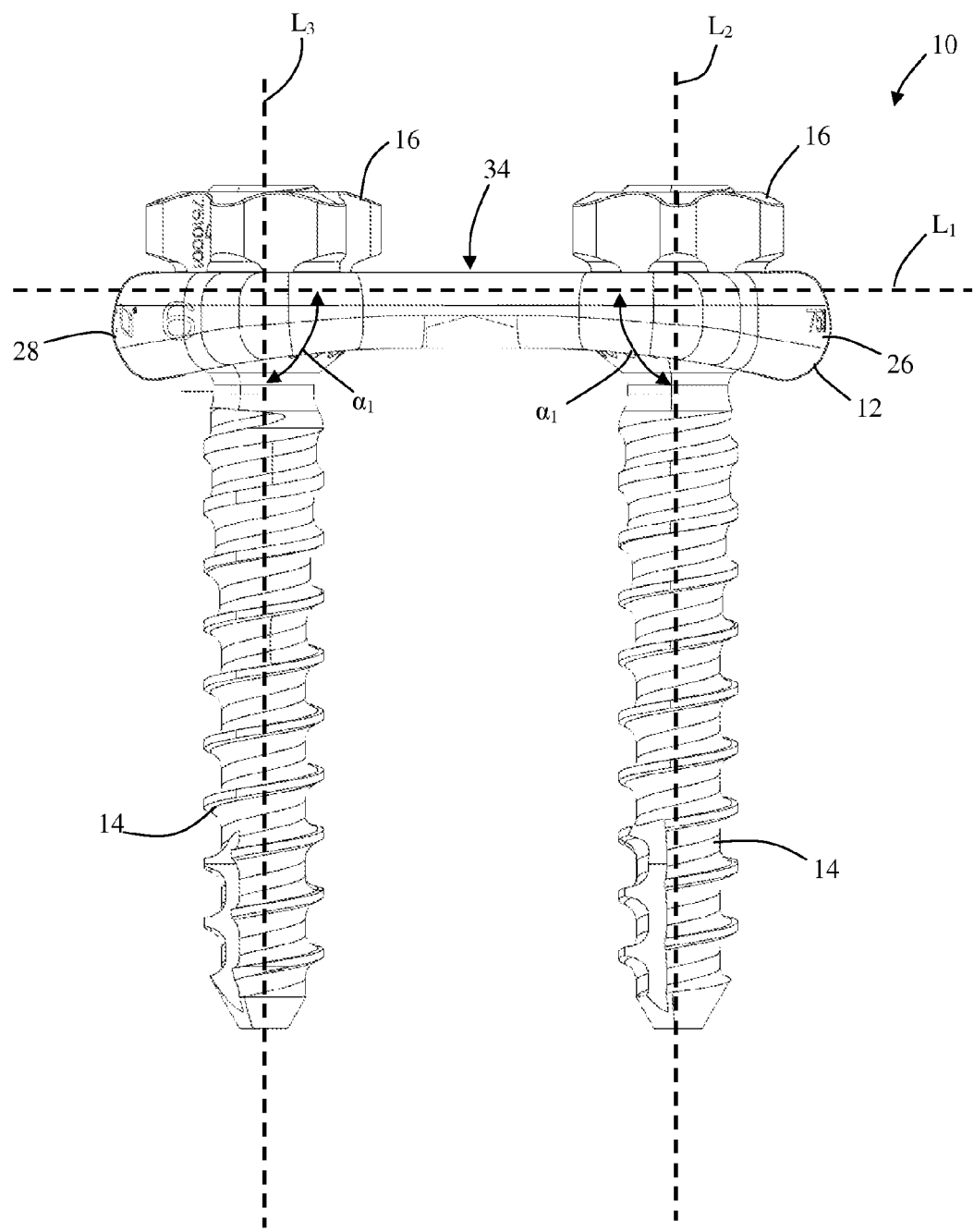
FIG. 20 is a front plan view of the assembled surgical fixation system of FIG. 2.
Figure 21:
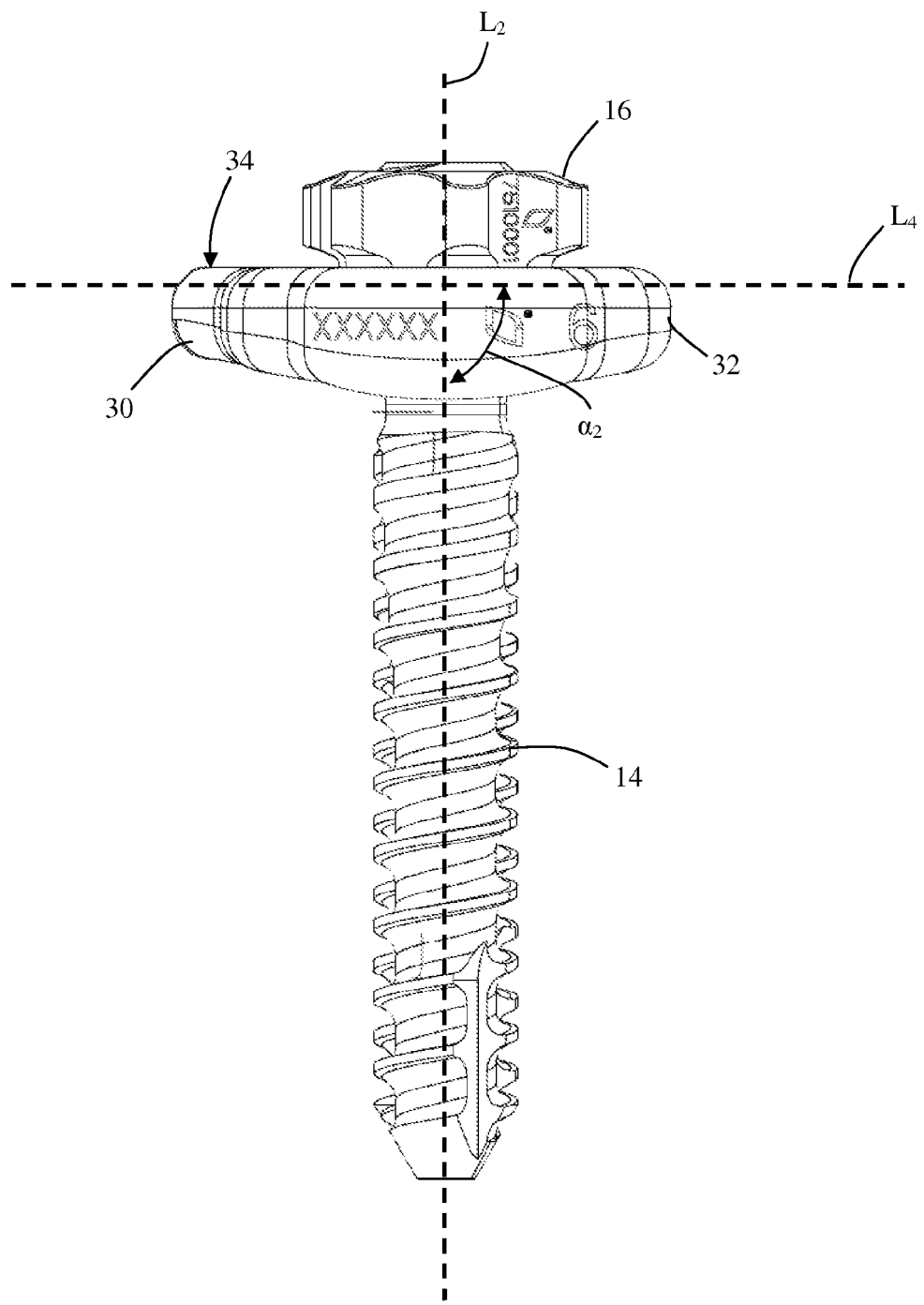
FIG. 21 is a side plan view of the assembled surgical fixation system of FIG. 2.

FIGS. 20 and 21 illustrate the positioning of the anchors 14 relative to one another and relative to the base plate 12. Referring to FIG. 20, the base plate 12 has a longitudinal axis (denoted by line $L_1$) extending through the base plate 12 from the first end 26 through the second end 28 and parallel to the generally planar top surface 34. The anchors 14 each have a longitudinal axis (denoted by lines $L_2$ and $L_3$) extending therethrough. Upon assembly, the anchors 14 are positioned such that their respective longitudinal axes $L_2$, $L_3$ are generally parallel to one another and generally perpendicular to axis $L_1$ of the base plate 12. In other words, the angle $\alpha_1$ between axes $L_1$ and $L_2$, and between axes $L_1$ and $L_3$, is approximately 90°. Similarly, as illustrated in FIG. 21, the angle $\alpha_2$ between axis $L_4$ (an axis extending laterally through base plate 12 between first and second sides 30, 32 and parallel to the generally planar top surface 34) and axis $L_2$ (the longitudinal axis of anchor 14) is also approximately 90°.

This disposition of the anchors 14 relative to the base plate 12 is significant for several reasons. First, the anchors 14 are driven into the vertebral bodies just inside of the endplates bordering the intervertebral space. This ensures that the anchors 14 are achieving significant cortical purchase within the vertebral bodies, allowing for a more secure fixation as compared with constructs that have significant purchase within cancellous bone. Moreover, the approximate 90° angulation of the anchors 14 enables a more direct approach to implantation than would be possible if the anchors 14 were divergent. This is a significant benefit when dealing with a minimally invasive operative corridor (e.g. through an incision approximately 1-2 inches wide before tissue distraction, and 3-4 inches wide post-distraction) in that the surgeon does not have to deal with an angled approach to the vertebral bodies that may not coincide with the angle of the established operative corridor. For example, the surgical fixation system 10 disclosed herein may be used in a direct lateral surgical procedure, in which the spine is approached laterally at a 90° angle relative to the patient's spine. Because the anchors 14 are implanted directly into the vertebrae at a 90° angle, no reestablishment of the operative corridor is necessary. Thus, the generally perpendicular orientation between the anchors 14 and the base plate 12 represents a significant advantage in implantation of the surgical fixation system 10 in terms of ease of use and incremental time involved in adding this supplemental fixation to a spinal fusion surgery. Although the 90° angle described above is the preferred angle insertion, a slight divergence (e.g. up to 6° of angulation) is possible without changing instrumentation, and thus is within the scope of the present invention.

Although shown in FIGS. 17-21 and described above as assembled in space, the surgical fixation system 10 of the present invention is assembled in situ during a surgical procedure. One such example is a spinal fusion surgery. As mentioned previously, the surgical fixation system 10 disclosed herein is optimally used in a direct lateral surgical procedure, in which the spine is approached laterally at approximately a 90° angle relative to the patient's spine. The first step in such a procedure is to create an operative corridor through the patient's skin and underlying musculature to the surgical target site, for example a symptomatic intervertebral disc located between first and second adjacent vertebral bodies. The specific technique involved in performing this step is shown and describe in commonly owned and co-pending U.S. patent application Ser. No. 10/967,668, filed on Oct. 18, 2004 and entitled "Surgical Access System and Related Methods," the entire contents of which are hereby incorporated by reference into this disclosure as if set forth fully herein.

A key component of the technique of establishing the operative corridor is the surgical retraction system 204 (FIG. 36). Notably, the surgical retraction system 204 includes a plurality of retractor blades 200, 202, and 206. The surgical retraction system 204 is introduced to the surgical target site in an initial "closed" position wherein the blades 200, 202, 206 are together form a generally cylindrical tubular member. Thereafter, the surgical retraction system 204 is moved to an "open" position (shown in FIG. 36) in which the retractor blades 200, 202, 206 are spread apart from one another, thereby establishing the operative corridor to the surgical target site. As the three blades 200, 202, 206 initially form a generally cylindrical tubular member in a closed position, each blade has a defined radius of curvature. This radius of curvature is approximately equal to the radius of curvature of the first and second ends 26, 28 of the base plate 12, as discussed above.

After establishment of the operative corridor to the surgical target site, the next step is to perform the necessary therapeutic technique to relieve the distress on the target disc space. For example, this may involve performing a partial or total discectomy—removing damaged or degenerative disc tissue from the intervertebral space and then inserting a spinal fusion implant such as a bone graft (e.g. allograft, autograft, or xenograft) or synthetic fusion cage (e.g. titanium and/or PEEK) into the space. One example of a synthetic spinal fusion implant that may be used is shown and described in commonly owned and co-pending U.S. patent application Ser. No. 11/093,409 filed on Mar. 29, 2005 and entitled "Systems and Methods for Spinal Fusion," the entire contents of which are hereby incorporated by reference into this disclosure as if set forth fully herein. These spinal fusion implants (natural or synthetic) may be used with or without additional fusion inducing materials, such as an orthopedic matrix containing for example (including but not limited to) calcium hydroxyapatite, bone morphogenic protein (BMP), demineralized bone matrix, collagen bone graft matrix (e.g. Formagraft®) and stem cell material (e.g. Osteocel®), or other fusion-promoting substances placed within the spaces of the implant, while the implant is advanced into the intervertebral space.

Figure 24:
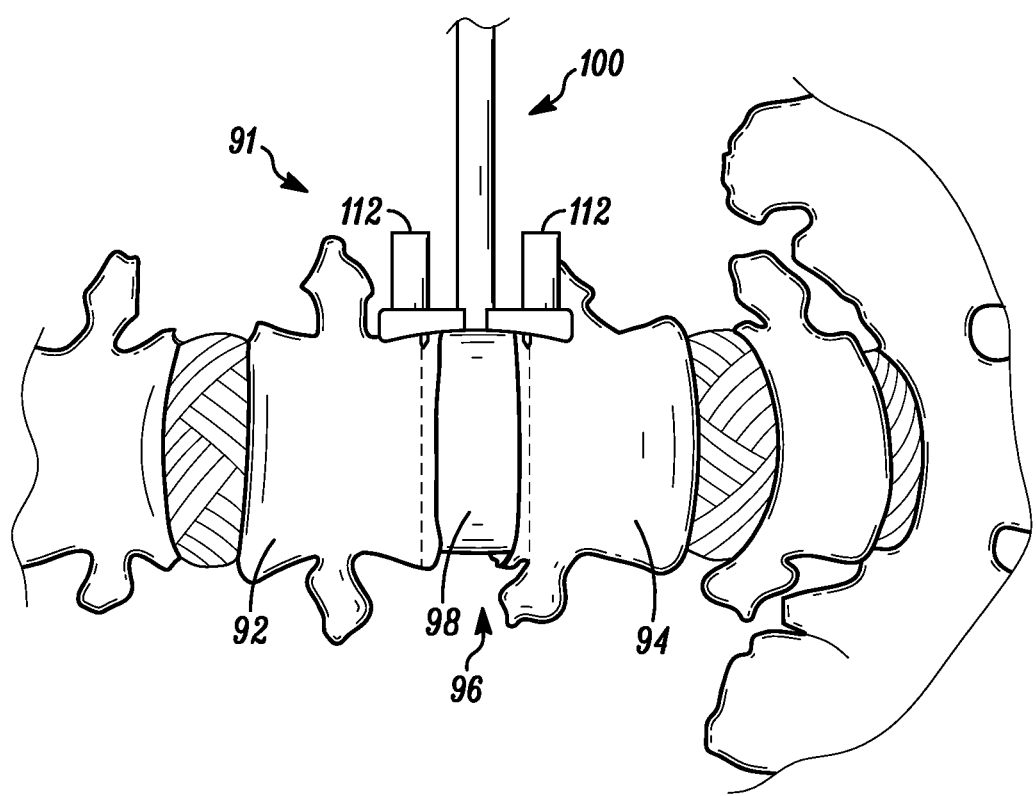
FIG. 24 is a side view of the drill guide of FIG. 22 in position along a lateral aspect of a spine.

After addressing the distressed disc space, the next step is to add supplemental fixation, if desired. In this case the surgical fixation system 10 of the present invention is implanted through the operative corridor within the surgical target site to help with the fusion process. The first step in implanting the surgical fixation system 10 is to implant the anchors 14 within the first and second vertebral bodies. Referring to FIG. 24, a surgical target site 91 is shown comprising a first vertebral body 92, a second vertebral body 94, and an intervertebral disc space 96 situated between the first and second vertebral bodies 92, 94. A spinal fusion implant 98 has been inserted into the disc space 96.

Figures 22, 23:
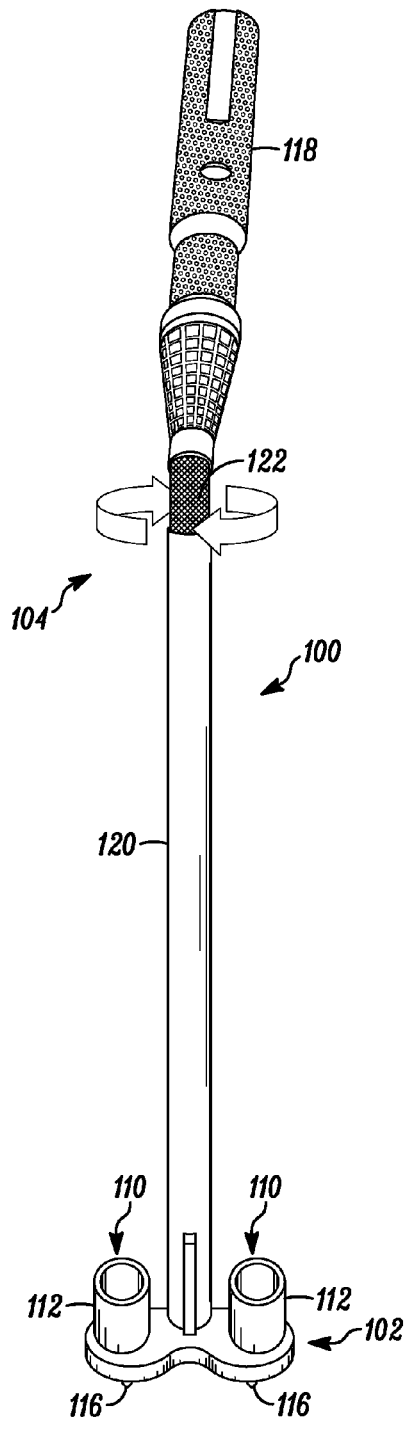
FIG. 22 is a perspective view of a drill guide for use with the surgical fixation system of FIG. 1 according to a further embodiment of the present invention.
FIG. 23 is a perspective view of the distal end of the drill guide of FIG. 22.

FIGS. 22-23 illustrate a guide member 100 for aiding in the proper placement of the anchors 14 within the vertebral bodies. The guide member 100 includes a guide plate 102 and an inserter 104. The guide plate 102 may be provided in any size suitable for the procedure, and the size and shape of the guide plate corresponds directly to the size and shape of the particular base plate 12 selected for the procedure. The guide plate 102 includes a top surface 106 and a bottom surface 108. The top surface 106 includes a pair of apertures 110 dimensioned to allow placement of the anchors 14 therethrough. The apertures 110 include generally cylindrical guide barrels 112 extending generally perpendicularly from the top surface 106 in order to provide stability for the various instruments (e.g. drills, taps, anchor inserters) that will be used through the apertures 110. The guide barrels 112 may be provided as separate parts that are inserted into the apertures 110, or in the alternative may be integrally formed with the guide plate 102. The top surface 106 further includes a threaded insertion aperture 114 positioned along the approximate midline of the guide plate 102. The bottom surface 108 is contoured similarly to the bottom surface 36 of the base plate 12 such that the bottom surface 108 is dimensioned to fit the anatomic contours of the vertebral bodies 92, 94. The bottom surface 108 further includes a pair of projections 116 provided to allow purchase into the vertebral bodies 92, 94 to stabilize the guide plate 102 during use (FIG. 24). The projections are located near the medial edges of the apertures 110 to help the user determine the precise location of the anchors 14.

The inserter 104 includes a handle portion 118, an outer tube 120, and shaft (not pictured) extending through the outer tube 120. The distal end of the shaft is threaded to facilitate engagement with the threaded insertion aperture 114 of the guide plate 102. The proximal end of the shaft includes gripping element 122 which may be turned by a user in a clockwise direction to facilitate the threaded engagement between the distal end of the shaft and the threaded insertion aperture 114.

Once the appropriate sized guide plate 102 is selected by the user, the inserter 104 and guide plate 102 are engaged as described above. The guide member 100 is then advanced along the operative corridor until it reaches the surgical target site 91. As shown in FIG. 24, the projections 116 on the bottom surface 108 of the guide plate 102 are inserted into vertebral bodies 92, 94 to provide stability for the guide member 100. The insertion locations for each of the projections 116 are within the cortical bone, at least 2 mm off of the endplates of each vertebral body 92, 94 immediately adjacent the disc space 96. The guide plate 102 is positioned directly over the implanted spinal fusion implant 98 with the guide barrels 112 generally equidistant from the endplates, as shown in FIG. 24. The relative positioning of the projections 116 and apertures 110 ensures proper location of the anchors 14 within the cortical bone of the vertebral bodies 92, 94. Specifically, the projections 116 are positioned such that they represent a line tangent to the major diameter of the anchor 14 at the point closest to the endplate. Thus, proper positioning of the projections 116 will ensure that there is at least 2 mm of cortical bone between the anchor 14 and the edge of the endplate. This is an important step due to the 90° insertion angle of the anchors 14. If the selected guide plate 102 is too small, then the anchors 14 will potentially breach the endplates and be at least partially exposed within the disc space 96, resulting in a less stable fixation.

Once the guide plate 102 is properly seated within the surgical target site 91, the surgeon proceeds with pilot hole formation to prepare the vertebral bodies 92, 94 for receiving the anchors 14. Formation of the pilot hole may be accomplished via a number of different techniques and instruments depending upon the surgeon's preference, including but not limited to using drills, taps, awls, etc. to create a pilot hole that is preferably undersized by 1 mm relative to the anchors 14 to be used in order to maximize the purchase of the anchors 14 within the bone.

Upon formation of the pilot hole, the anchors 14 are inserted through the guide barrels 112, apertures 110 and into the bone. FIGS. 25-28 illustrate an example of a driver 124 suitable for use with the anchors 14. The driver 124 includes a handle 126, an inner shaft 128, an outer sleeve 130, a locking element 132, and an alignment sleeve 134. The handle 124 is contoured to allow for comfortable use by a surgeon. The inner shaft 126 is a generally straight elongated member that extends in a distal direction from the handle 124. The inner shaft 126 includes a distal tip 136 that having a shape corresponding to that of the recess 66 located on the head 20 of the anchor 14. The outer sleeve 130 extends substantially along the length of the inner shaft 128 and includes a distal tip 138 including an inner threaded region dimensioned to threadedly engage the threadform 64 of the head 20 of the anchor 14. The outer sleeve 130 further includes a proximal gripping element 140 to enable the user to rotate the outer sleeve 130 in either a clockwise or counterclockwise direction to facilitate the engagement of the outer sleeve 130 with the anchor 14. The locking element 132 is positioned proximally of the outer sleeve 130, between the outer sleeve 130 and handle 126 and is dimensioned to slideably engage the outer sleeve 130 in order to lock the outer sleeve 130 in position once engaged to the anchor 14. The alignment sleeve 134 is positioned about the distal region of the outer sleeve 130, and is configured to slide in a distal direction until it receives substantially all of the anchor 14 within the inner lumen 142. Inner lumen is sized and dimensioned to slideably engage the outside of the guide barrels 112 of the guide plate 102.

In use, once the appropriate sized anchors 14 are identified, the user engages the anchor 14 to the driver 124. This is accomplished by first inserting the distal tip 136 of the inner shaft into the recess 66 located on the head 20 of the anchor 14. The outer sleeve 130 is then rotated (by a user engaging gripping element 140) in a clockwise direction to advance the outer sleeve 130 in a distal direction. As this is occurring, the inner threaded region of the distal tip 138 threadedly engages the threadform 64 of the head 20 of the anchor 12. Once fully threadedly engaged, the outer sleeve 130 is locked in place by distally sliding the locking element 132 into position. The anchor 14 is now locked to the driver 124 and is ready to be inserted into bone. At this point the alignment sleeve 134 is slid distally into position (FIG. 28) to prepare the driver 124 for engagement with the guide barrels 112.

Figures 29, 30:
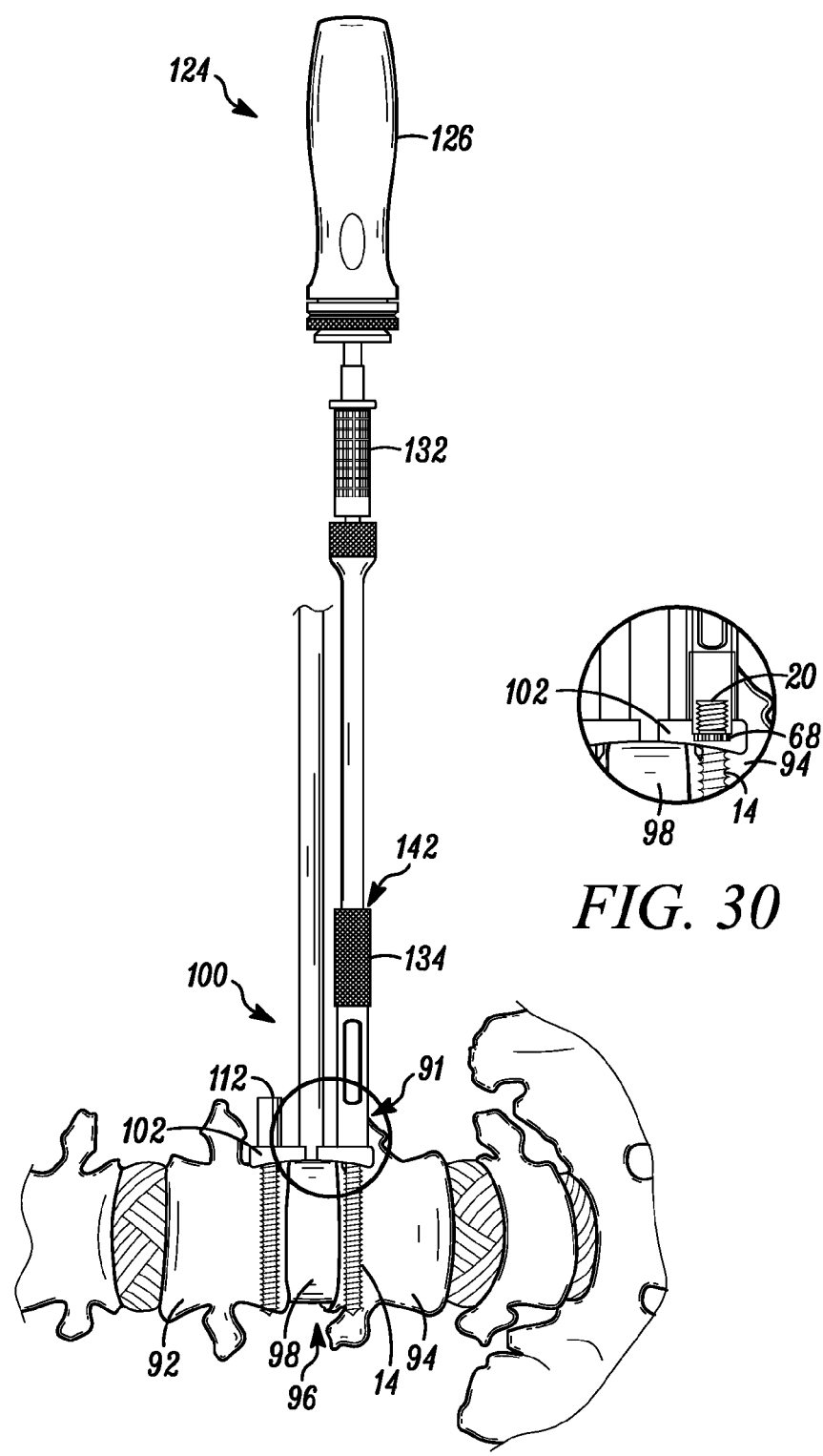
FIG. 29 is a side plan view of the screw inserter of FIG. 25 used in combination with the drill guide of FIG. 22.
FIG. 30 is a cross-sectional view of the screw inserter and drill guide combination of FIG. 29.

Referring to FIGS. 29 and 30, to ensure proper placement of the anchors 14 into the bone, the driver 124 is positioned over the guide barrel 112 such that the guide barrel 112 is received within the inner lumen 142 of the alignment sleeve 134. This ensures proper angulation of the anchors 14 is maintained throughout the insertion process. The anchor 14 is advanced into the vertebral body 94 by rotating the handle 126 in a clockwise direction. It is contemplated that the handle 126 may be provided with a ratchet-like mechanism to improve the ease of insertion of the anchor 14. When the anchor 14 is fully seated within the vertebral body 94, the chocks 68 of the anchor 14 are fully exposed over the vertebral body 94. This will ensure proper engagement of the base plate 12 with the anchor 14. After one anchor 94 is fully seated within vertebral body 94, the driver 124 is disengaged from the head 20 of the anchor 14, for example by first sliding the locking element 132 in a proximal direction, rotating the outer sleeve 130 in a counterclockwise direction to disengage the threads from the head 20 of the anchor 14, and removing the driver 124 from the operative corridor. The process is then repeated with respect to vertebral body 92.

Figure 31:
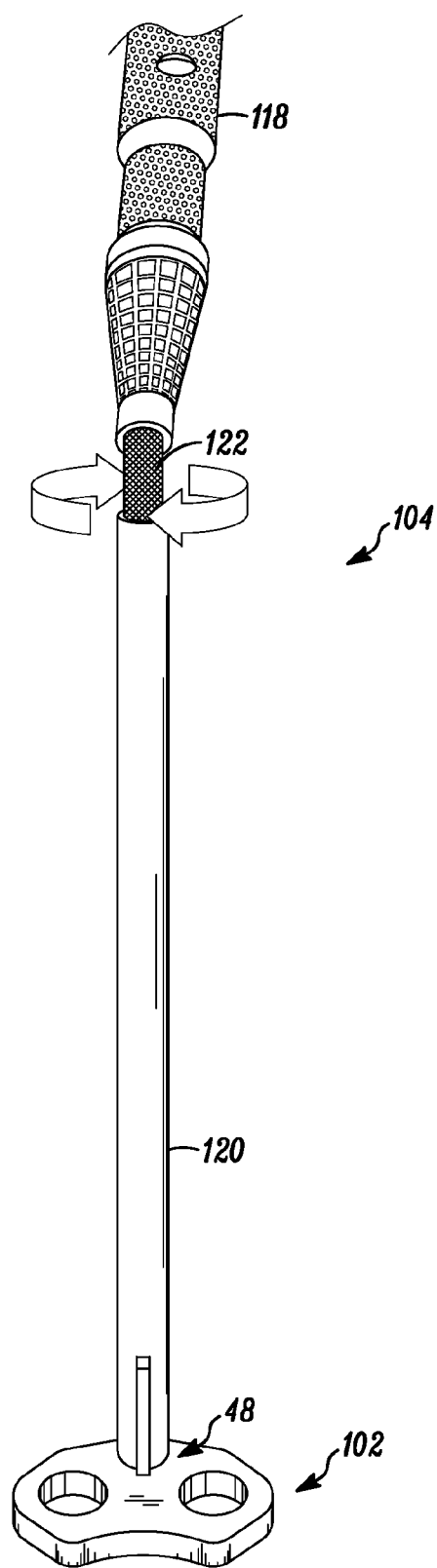
FIG. 31 is a perspective view of the bone plate of FIG. 3 engaged with a plate inserter according to one embodiment of the present invention.
Figure 32:
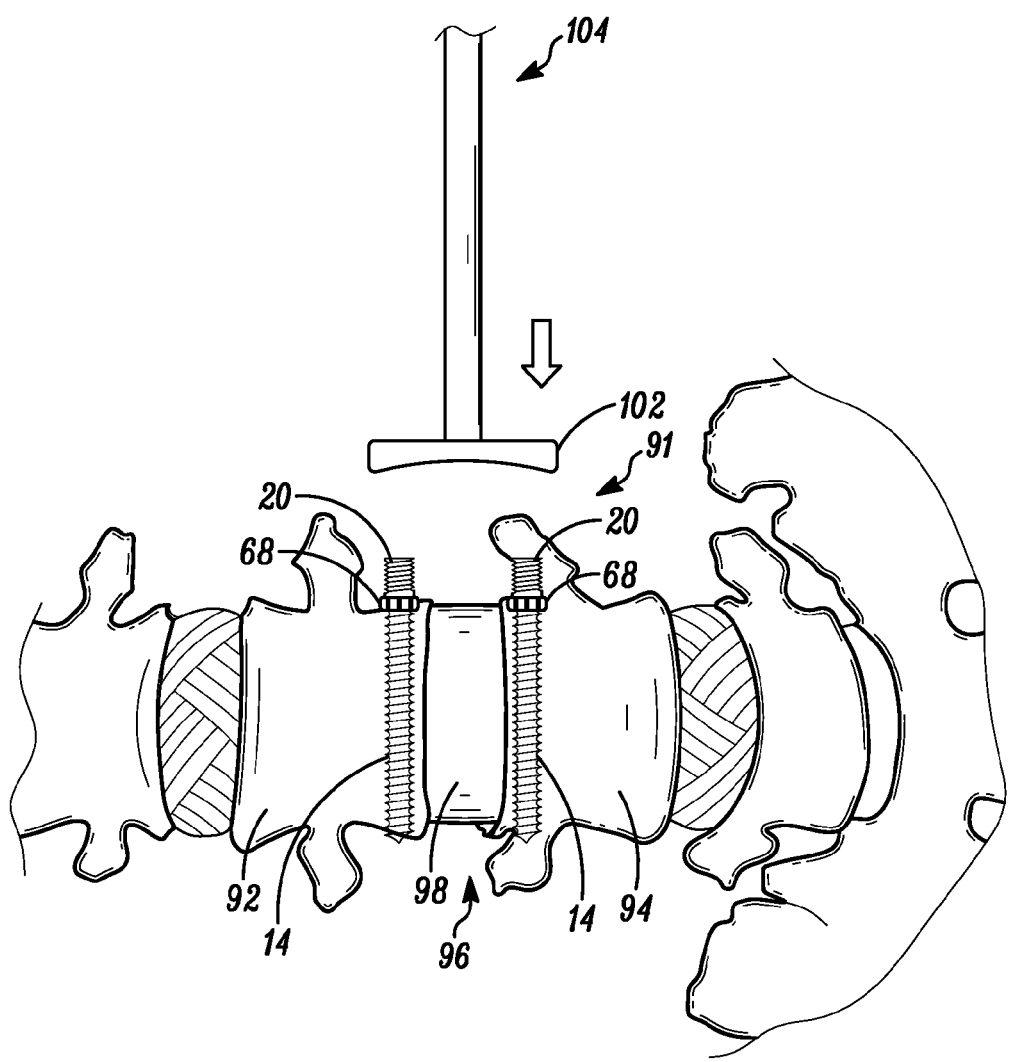
FIG. 32 is a side plan view of the bone plate of FIG. 3 being implanted in situ over a pair of implanted bone screws.
Figure 33:
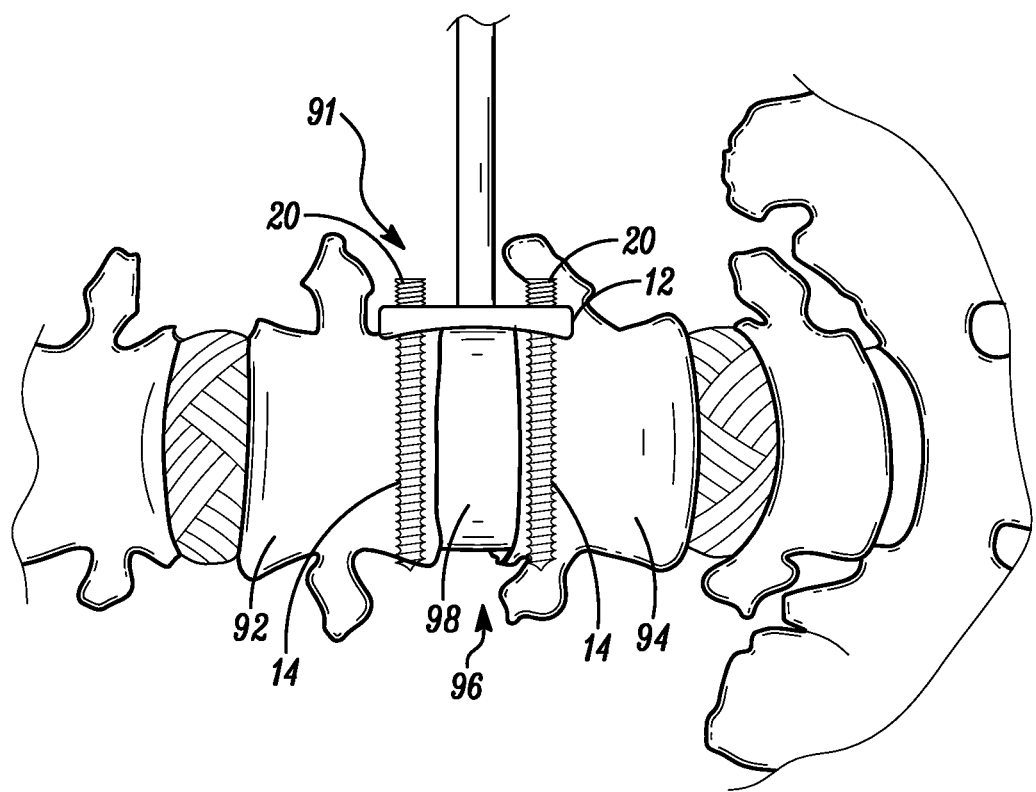
FIG. 33 is a side plan view of the bone plate of FIG. 3 fully implanted in situ over a pair of implanted bone screws.

Referring to FIGS. 31-33, once both anchors 14 are properly implanted within the vertebral bodies 92, 94 (e.g. FIG. 32), the base plate 12 is implanted within the surgical target site 91. To accomplish this, the base plate 12 is first engaged with an inserter to facilitate introduction into the surgical target site 91. The inserter for this task may be the same as the inserter 104 described above in relation to the guide member 100. The inserter 104 includes a handle portion 118, an outer tube 120, and shaft (not pictured) extending through the outer tube 120. The distal end of the shaft is threaded to facilitate engagement with the threaded insertion aperture 48 of the base plate 12. The proximal end of the shaft includes gripping element 122 which may be turned by a user in a clockwise direction to facilitate the threaded engagement between the distal end of the shaft and the threaded insertion aperture 48.

Referring to FIG. 32, once the base plate 12 is engaged with the inserter 104, the base plate 12 is advanced along the operative corridor toward the surgical target site 91. Referring to FIG. 33, the base plate 12 is positioned such that the heads 20 of the anchors 14 extend beyond the base plate 12 and also such that the chocks 68 are engaged with the contoured periphery 44 of the second recess 42 of the lower surface 36 of the base plate 12 (e.g. FIG. 19).

Referring to FIG. 34, upon seating of the base plate 12 on the anchors 14, the locking elements 16 are applied to secure the base plate 12 in place and complete assembly of the surgical fixation system 10. A locking element inserter 144 is provided to further this purpose. The locking element inserter 144 includes a handle (not shown), an elongated shaft 146, and a distal engagement end 148. The distal engagement end 148 includes a plurality tangs 150 dimensioned to engage the recesses 90 of the locking element 16. Once the locking element 16 is seated within the distal engagement end 148, the locking element 16 is advanced into the surgical target site 91 and threaded onto the head 20 of the anchor 14. As described earlier, as the locking element 16 is advanced onto the head 20 of the anchor 14 (via the engagement between threads 86 of the locking element 16 and threads 64 of the head 20), the lower exterior portion 84 will be received into the first recess 38 of the base plate 12. The lower exterior portion 84 will interface with the sloped surface 40 and exert a force on the base plate 12, essentially sandwiching the base plate 12 between the anchor 14 and the locking element 16. This process is repeated for the other anchor 14. At this point the construct is fully assembled and locked in place.

Referring to FIG. 36, at this stage, the surgical fixation system 10 is fully assembled in situ and implanted into a surgical target site. The anchors 14 are seated within the vertebral bodies 92, 94. The base plate 12 is seated upon the anchors 14 and locked in place with the locking elements 16. A spinal fusion implant 98 is implanted within the intervertebral space 96, and the disc height is restored. At this point, the surgical retraction system 204, including retractor blades 200, 202 may be closed and removed from the patient. This effective closes the operative corridor. The procedure being completed, the incision is stitched up.

The base plate 12, anchors 14, and/or lock nuts 16 may be formed of any material suitable to provide rigid fixation between two bony segments. The base plate 12, anchors 14, and lock nuts 16 may all be formed of a biocompatible metal, such as titanium, for example. The base plate 12 may be provided with any size necessary to complete the desired spinal fixation. By way of example only, the anchors 14 may be provided with a length in the range of about 25 mm to about 65 mm.

While this invention has been described in terms of a best mode for achieving this invention's objectives, it is understood by those skilled in the art that variations may be accomplished in view of these teachings without deviating from the spirit or scope of the invention.

The invention claimed is:

1. A system for fixing a first bone segment to a second bone segment, comprising:
   a base plate having a first end, a second end, first and second sides extending between the first and second ends, and first and second surfaces each extending between the first end, second end, first side, and second side, the first side having a convexly curved portion and the second side having a concavely curved portion, the first and second surfaces separated by a thickness of the base plate, the base plate including a first fixation aperture adjacent the first end and a second fixation aperture adjacent the second end, the first and second fixation apertures each dimensioned to receive at least a portion of a fixation element extending therethrough, each of the first and second fixation apertures extending through a recess formed in the second surface of the base plate, the recesses having a periphery, the periphery having an edge face, the entire edge face of the periphery of the recesses comprised of vertically-oriented chocks, the base plate further including a single insertion aperture adjacent the convexly curved portion of the first side and extending between the first and second surfaces and dimensioned to receive at least a portion of an insertion instrument therethrough, the insertion aperture comprising a recess formed within the first surface and a threaded aperture extending between the recess and the second surface;

a plurality of fixation elements, the fixation elements including a first threaded portion and second threaded portion separated by an intermediate portion with an edge face, the edge face of the intermediate portion including a plurality of vertically-oriented chocks configured to engage the vertically-oriented chocks of the edge face of the periphery of the recesses of said second surface of the base plate; and a plurality of locking elements configured to threadedly engage the first threaded portion of the fixation elements.

2. The system of claim 1, wherein at least one of the first and second fixation apertures comprises an elongated slot.

3. The system of claim 1, wherein the second threaded portion comprises an elongated shaft having a helical thread configured to provide purchase within bone.

4. The system of claim 1, wherein the first and second ends are generally rounded.

5. The system of claim 1, further comprising a middle portion positioned in between the first and second ends, the middle portion having a thickness dimension that is less than the thickness dimensions of each of the first and second ends.

6. The system of claim 1, wherein the first surface is generally planar.

7. The system of claim 6, wherein the second surface has a generally concave curvature.

8. The system of claim 1, wherein the second surface is configured to contact bone.

9. The system of claim 1, wherein the first and second bone segments comprise first and second vertebral bodies of a spine.

* * * * *